United States Patent
Ichinose

(10) Patent No.: US 12,249,069 B2
(45) Date of Patent: Mar. 11, 2025

(54) LEARNING DEVICE, LEARNING METHOD, LEARNING PROGRAM, INFORMATION PROCESSING APPARATUS, INFORMATION PROCESSING METHOD, AND INFORMATION PROCESSING PROGRAM

(71) Applicant: FUJIFILM Corporation, Tokyo (JP)

(72) Inventor: Akimichi Ichinose, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 359 days.

(21) Appl. No.: 17/849,692

(22) Filed: Jun. 26, 2022

(65) Prior Publication Data

US 2023/0030794 A1 Feb. 2, 2023

(30) Foreign Application Priority Data

Jul. 29, 2021 (JP) .................................. 2021-124683

(51) Int. Cl.
  *G06T 7/00* (2017.01)
  *G06V 10/82* (2022.01)
  *G16H 50/20* (2018.01)

(52) U.S. Cl.
  CPC ............ *G06T 7/0012* (2013.01); *G06V 10/82* (2022.01); *G16H 50/20* (2018.01); *G06T 2207/20081* (2013.01); *G06T 2207/20084* (2013.01); *G06T 2207/30096* (2013.01)

(58) Field of Classification Search
  CPC ....... G06T 7/0012; G16H 50/20; G06V 10/82
  See application file for complete search history.

(56) References Cited

U.S. PATENT DOCUMENTS

| | | | |
|---|---|---|---|
| 2018/0204111 A1* | 7/2018 | Zadeh | G06V 10/764 |
| 2020/0364507 A1* | 11/2020 | Berry | G06F 18/217 |
| 2021/0090694 A1* | 3/2021 | Colley | G16H 15/00 |
| 2021/0118035 A1* | 4/2021 | Misawa | G06N 5/04 |
| 2022/0014807 A1* | 1/2022 | Lin | G06V 20/635 |
| 2022/0121884 A1* | 4/2022 | Zadeh | G06N 3/006 |
| 2023/0005178 A1* | 1/2023 | Liu | G06N 3/0442 |

OTHER PUBLICATIONS

Elad Hoffer et al., "Deep Metric Learning Using Triplet Network," arXiv:1412.6622v1, Dec. 2014, pp. 1-6.
Liwei Wang et al., "Learning Two-Branch Neural Networks for Image-Text Matching Tasks," arXiv:1704.03470v1, Apr. 2017, pp. 1-14.

* cited by examiner

*Primary Examiner* — David Bilodeau
(74) *Attorney, Agent, or Firm* — JCIPRNET

(57) ABSTRACT

A processor derives a first feature amount for an object included in an image by a first neural network, and derives a second feature amount for a sentence including description of an object by a second neural network. The processor acquires each of a first attribute, which is an attribute of the object included in the image, and a second attribute, which is an attribute of the sentence. The processor trains the first and second neural networks such that, in a feature space to which first and second feature amounts belong, as relevance of a combination of the first and the second attributes is higher a distance between the derived first feature amount and second feature amount is smaller.

14 Claims, 17 Drawing Sheets

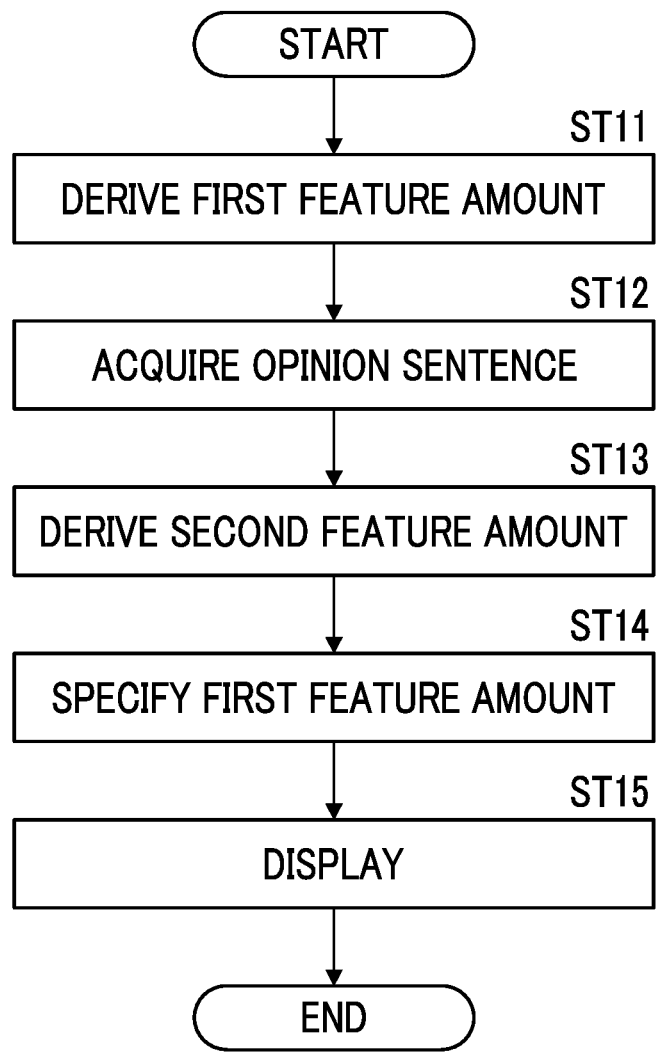

LEARNING DEVICE, LEARNING METHOD, LEARNING PROGRAM, INFORMATION PROCESSING APPARATUS, INFORMATION PROCESSING METHOD, AND INFORMATION PROCESSING PROGRAM

CROSS REFERENCE TO RELATED APPLICATIONS

The present application claims priority under 35 U.S.C. § 119 to Japanese Patent Application No. 2021-124683 filed on Jul. 29, 2021. The above application is hereby expressly incorporated by reference, in its entirety, into the present application.

BACKGROUND

Technical Field

The present disclosure relates to a learning device, a learning method, a learning program, an information processing apparatus, an information processing method, and an information processing program.

Related Art

A method of constructing a feature space to which a feature amount, such as a feature vector, extracted from an image belongs using a trained model that has been subjected to machine learning by deep learning or the like has been proposed. For example, Deep metric learning using Triplet network, Elad Hoffer et al., 20 Dec. 2014, arXiv: 1412.6622 proposes a method of training a trained model such that the feature amounts of the images belonging to the same class get close to each other in the feature space and the feature amounts of the images belonging to different classes are separated from each other in the feature space. In addition, there is also known a technology of associating a feature amount extracted from an image with a feature amount extracted from a sentence based on a distance in a feature space (see Learning Two-Branch Neural Networks for Image-Text Matching Tasks, Liwei Wang et al., 11 Apr. 2017, arXiv: 1704.03470).

As disclosed in Learning Two-Branch Neural Networks for Image-Text Matching Tasks, Liwei Wang et al., 11 Apr. 2017, arXiv: 1704.03470, in order to accurately train the trained model that associates the image with the sentence, a large amount of teacher data in which a feature included in the image and a feature described in the sentence are associated with each other is required. However, due to the limited number of images and sentences, it may be difficult to prepare a large amount of teacher data. In particular, in the field of medical image analysis, since the number of medical images is limited, it is difficult to construct the trained model capable of associating the image with the sentence with high accuracy.

SUMMARY OF THE INVENTION

The present disclosure has been made in view of the above circumstances, and is to enable association between an image and a sentence with high accuracy.

A learning device according to the present disclosure comprises at least one processor, in which the processor derives a first feature amount for an object included in an image by a first neural network, derives a second feature amount for a sentence including description of an object by a second neural network, acquires each of a first attribute, which is an attribute of the object included in the image, and a second attribute, which is an attribute of the sentence, and constructs a first derivation model that derives a feature amount for the object included in the image and a second derivation model that derives a feature amount for the sentence including the description of the object by training the first neural network and the second neural network such that, in a feature space to which the first feature amount and the second feature amount belong, as relevance of a combination of the first attribute and the second attribute is higher, a distance between the derived first feature amount and second feature amount is smaller than a case in which the relevance of the combination of the first attribute and the second attribute is low.

It should be noted that, in the learning device according to the present disclosure, the first attribute may be a position of the object in the image, and the second attribute may be a position of the object described in the sentence.

In addition, in the learning device according to the present disclosure, the first attribute may be a property of the object included in the image, and the second attribute may be a property of the object described in the sentence.

In addition, in the learning device according to the present disclosure, the processor may acquire the first attribute and the second attribute based on a co-occurrence relationship of a text representing the property.

In addition, in the learning device according to the present disclosure, the processor may train the first neural network and the second neural network such that the distance between the derived first feature amount and second feature amount in the feature space is reduced in a case in which the object included in the image and the object described in the sentence correspond to each other, and may train the first neural network and the second neural network such that the distance between the derived first feature amount and second feature amount in the feature space is increased in a case in which the object included in the image and the object described in the sentence do not correspond to each other.

In addition, in the learning device according to the present disclosure, the image may be a medical image, the object included in the image may be a lesion included in the medical image, and the sentence may be an opinion sentence in which an opinion about the lesion is described.

A first information processing apparatus according to the present disclosure comprises at least one processor, in which the processor derives a first feature amount for one or more objects included in a target image by the first derivation model constructed by the learning device according to the present disclosure, derives a second feature amount for one or more target sentences including description of an object by the second derivation model constructed by the learning device according to the present disclosure, specifies the first feature amount corresponding to the second feature amount based on a distance between the derived first feature amount and second feature amount in a feature space, and displays the object from which the specified first feature amount is derived, in distinction from other regions in the target image.

A second information processing apparatus according to the present disclosure comprises at least one processor, in which the processor receives input of a target sentence including description of an object, derives a second feature amount for the input target sentence by the second derivation model constructed by the learning device according to the present disclosure, refers to a database in which a first feature amount for one or more objects included in a plurality of reference images, which is derived by the first derivation model constructed by the learning device according to the present disclosure, is associated with each of the reference images, to specify at least one first feature amount corresponding to the second feature amount based on a distance between the first feature amounts for the plurality of reference images and the derived second feature amount in a feature space, and specifies the reference image associated with the specified first feature amount.

A learning method according to the present disclosure comprises deriving a first feature amount for an object included in an image by a first neural network, deriving a second feature amount for a sentence including description of an object by a second neural network, acquiring each of a first attribute, which is an attribute of the object included in the image, and a second attribute, which is an attribute of the sentence, and constructing a first derivation model that derives a feature amount for the object included in the image and a second derivation model that derives a feature amount for the sentence including the description of the object by training the first neural network and the second neural network such that, in a feature space to which the first feature amount and the second feature amount belong, as relevance of a combination of the first attribute and the second attribute is higher, a distance between the derived first feature amount and second feature amount is smaller than a case in which the relevance of the combination of the first attribute and the second attribute is low.

A first information processing method according to the present disclosure comprises deriving a first feature amount for one or more objects included in a target image by the first derivation model constructed by the learning method according to the present disclosure, deriving a second feature amount for one or more target sentences including description of an object by the second derivation model constructed by the learning method according to the present disclosure, specifying the first feature amount corresponding to the second feature amount based on a distance between the derived first feature amount and second feature amount in a feature space, and displaying the object from which the specified first feature amount is derived, in distinction from other regions in the target image.

A second information processing method according to the present disclosure comprises receiving input of a target sentence including description of an object, deriving a second feature amount for the input target sentence by the second derivation model constructed by the learning method according to the present disclosure, referring to a database in which a first feature amount for one or more objects included in a plurality of reference images, which is derived by the first derivation model constructed by the learning method according to the present disclosure, is associated with each of the reference images, to specify at least one first feature amount corresponding to the second feature amount based on a distance between the first feature amounts for the plurality of reference images and the derived second feature amount in a feature space, and specifying the reference image associated with the specified first feature amount.

It should be noted that the learning method, and the first and second information processing methods according to the present disclosure may be provided as a program to be executed by a computer.

According to the present disclosure, it is possible to associate the image with the sentence with a high accuracy.

BRIEF DESCRIPTION OF THE DRAWINGS

FIG. 14 is a flowchart showing information processing performed in the first embodiment.

FIG. 15 is a diagram showing an example of a co-occurrence relationship.

DETAILED DESCRIPTION

Figure 1:
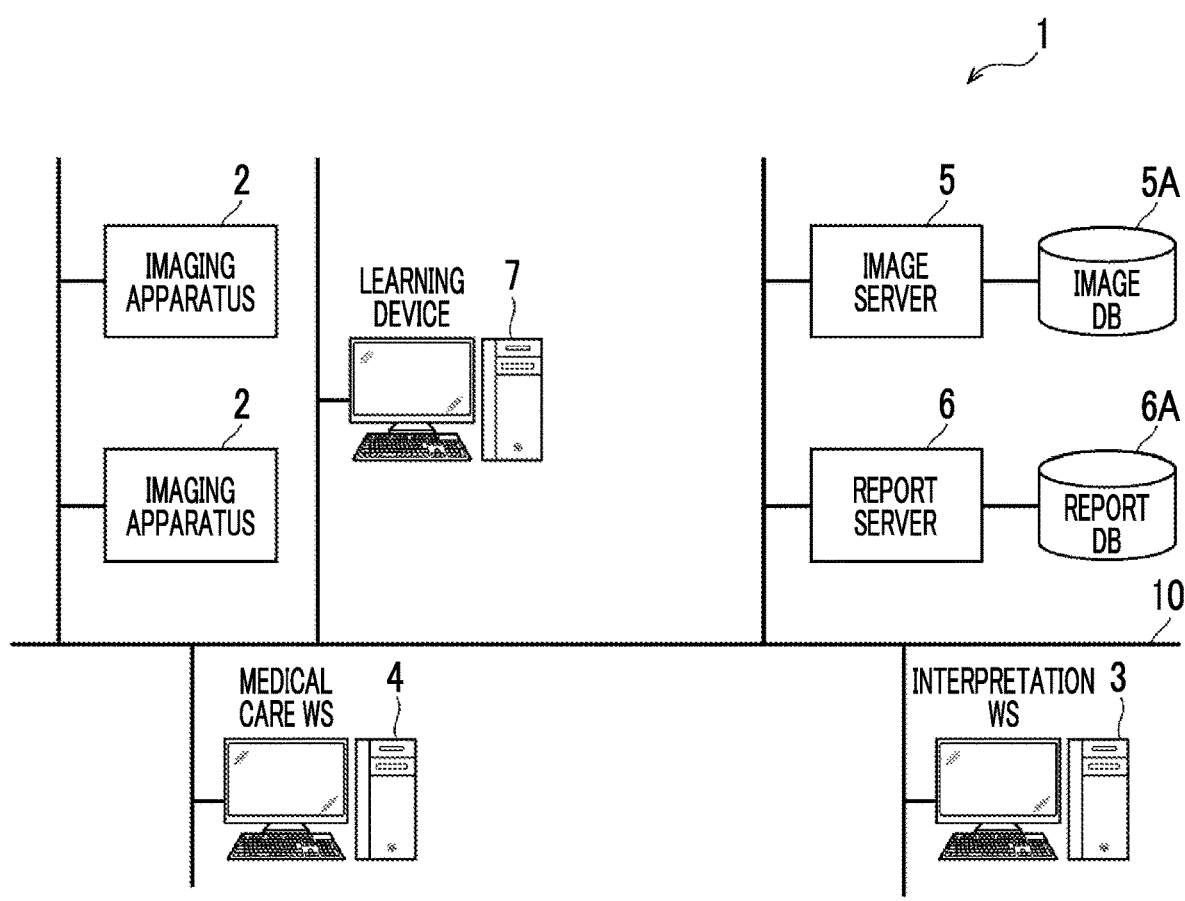
FIG. 1 is a diagram showing a schematic configuration of a medical information system to which a learning device and an information processing apparatus according to a first embodiment of the present disclosure are applied.

In the following, embodiments of the present disclosure will be described with reference to the drawings. First, a configuration of a medical information system to which a learning device and an information processing apparatus according to a first embodiment of the present disclosure are applied will be described. FIG. 1 is a diagram showing a schematic configuration of a medical information system 1. The medical information system 1 shown in FIG. 1 is a system that performs imaging of an examination target part of a patient who is a subject, the storage of a medical image acquired by imaging, the interpretation of the medical image and the creation of an interpretation report by an interpreter, and viewing of the interpretation report and the detailed observation of the medical image of an interpretation target by the doctor of the medical care department which is a request source, based on an examination order from a doctor of a medical care department by using a known ordering system.

As shown in FIG. 1, the medical information system 1 has a configuration in which a plurality of imaging apparatuses 2, a plurality of interpretation work stations (WSs) 3, a medical care WS 4, an image server 5, an image database (DB) 5A, a report server 6, a report DB 6A, and a learning device 7 are connected via a wired or wireless network 10 to be able to communicate with each other.

Each device is a computer on which an application program for functioning as a component of the medical information system 1 is installed. The application program is recorded in a recording medium, such as a digital versatile disc (DVD) and a compact disc read only memory (CD-ROM), is distributed, and is installed in the computer from the recording medium. Alternatively, the application program is stored in a storage device of a server computer connected to the network 10 or in a network storage in a state of being accessible from the outside, and is downloaded and installed in the computer in response to the request.

The imaging apparatus 2 is an apparatus (modality) that generates the medical image representing a diagnosis target part by imaging the diagnosis target part of the patient. Specifically, the imaging apparatus 2 is a simple X-ray imaging apparatus, a CT apparatus, an MRI apparatus, a positron emission tomography (PET) apparatus, and the like. The medical image generated by the imaging apparatus 2 is transmitted to the image server 5 and is then stored in the image DB 5A.

The interpretation WS 3 is a computer used by, for example, the interpreter of a radiology department to perform the interpretation of the medical image and the creation of the interpretation report, and encompasses the information processing apparatus (details will be described below) according to the present embodiment. In the interpretation WS 3, a viewing request for the medical image to the image server 5, various types of image processing for the medical image received from the image server 5, displaying of the medical image, and an input reception of an opinion sentence relating to the medical image are performed. In addition, in the interpretation WS 3, analysis processing of the medical image, support for creating the interpretation report based on the analysis result, a registration request and a viewing request for the interpretation report to the report server 6, and displaying of the interpretation report received from the report server 6 are performed. These types of processing are performed by the interpretation WS 3 executing a software program for each processing.

The medical care WS 4 is a computer used by the doctor of the medical care department to perform the detailed observation of the image, viewing of the interpretation report, the creation of an electronic medical record, and the like, and is composed of a processing apparatus, a display device, such as a display, and an input device, such as a keyboard and a mouse. In the medical care WS 4, the viewing request for the image to the image server 5, displaying of the image received from the image server 5, the viewing request for the interpretation report to the report server 6, and displaying of the interpretation report received from the report server 6 are performed. These types of processing are performed by the medical care WS 4 executing a software program for each processing.

The image server 5 is a server in which a software program providing a function of a database management system (DBMS) to a general-purpose computer is installed. In addition, the image server 5 comprises a storage constituting the image DB 5A. This storage may be a hard disk device connected to the image server 5 by a data bus, or may be a disk device connected to a network attached storage (NAS) and a storage area network (SAN) connected to the network 10. In addition, in a case in which the image server 5 receives the registration request of the medical image from the imaging apparatus 2, the image server 5 arranges the medical image in a format for a database and registers the arranged medical image in the image DB 5A.

In the image DB 5A, image data of the medical image acquired in the imaging apparatus 2 and accessory information are registered. The accessory information includes, for example, an image identification (ID) for identifying an individual medical image, a patient ID for identifying the patient, an examination ID for identifying the examination, a unique identification (UID) assigned to each medical image, an examination date and an examination time at which each medical image is generated, a type of imaging apparatus used in the examination to acquire each medical image, patient information, such as a name, an age, and a gender of the patient, an examination part (imaging part), imaging information (imaging protocol, imaging sequence, imaging method, imaging condition, use of contrast agent, and the like), and information, such as a series number or a collection number in a case in which a plurality of medical images are acquired in one examination. In addition, in the present embodiment, a first feature amount of the medical image derived as described below in the interpretation WS 3 is registered in the image DB 5A in association with the medical image.

In addition, in a case in which the viewing request from the interpretation WS 3 and the medical care WS 4 is received via the network 10, the image server 5 searches for the medical image registered in the image DB 5A and transmits the searched medical image to the interpretation WS 3 and the medical care WS 4 that are request sources.

The report server 6 incorporates the software program that provides the function of the database management system to the general-purpose computer. In a case in which the registration request for the interpretation report from the interpretation WS 3 is received, the report server 6 arranges the interpretation report in the format for a database, and registers the arranged interpretation report in the report DB 6A.

In the report DB 6A, a large number of interpretation reports including the opinion sentences created by the interpreter using the interpretation WS 3 are registered. The interpretation report may include, for example, information, such as the medical image of the interpretation target, the image ID for identifying the medical image, an interpreter ID for identifying the interpreter who performs the interpretation, a lesion name, positional information of the lesion, and a property of the lesion. In the present embodiment, the interpretation report and one or more medical images for which the interpretation report is created are associated with each other and registered in the report DB 6A.

In addition, in a case in which the viewing request for the interpretation report is received from the interpretation WS 3 and the medical care WS 4 via the network 10, the report server 6 searches for the interpretation report registered in the report DB 6A, and transmits the searched interpretation report to the interpretation WS 3 and the medical care WS 4, which are the request sources.

The network 10 is a wired or wireless local area network that connects various devices in a hospital. In a case in which the interpretation WS 3 is installed in another hospital or clinic, the network 10 may have a configuration in which the local area networks of respective hospitals are connected to each other via the Internet or a dedicated circuit.

Figure 2:
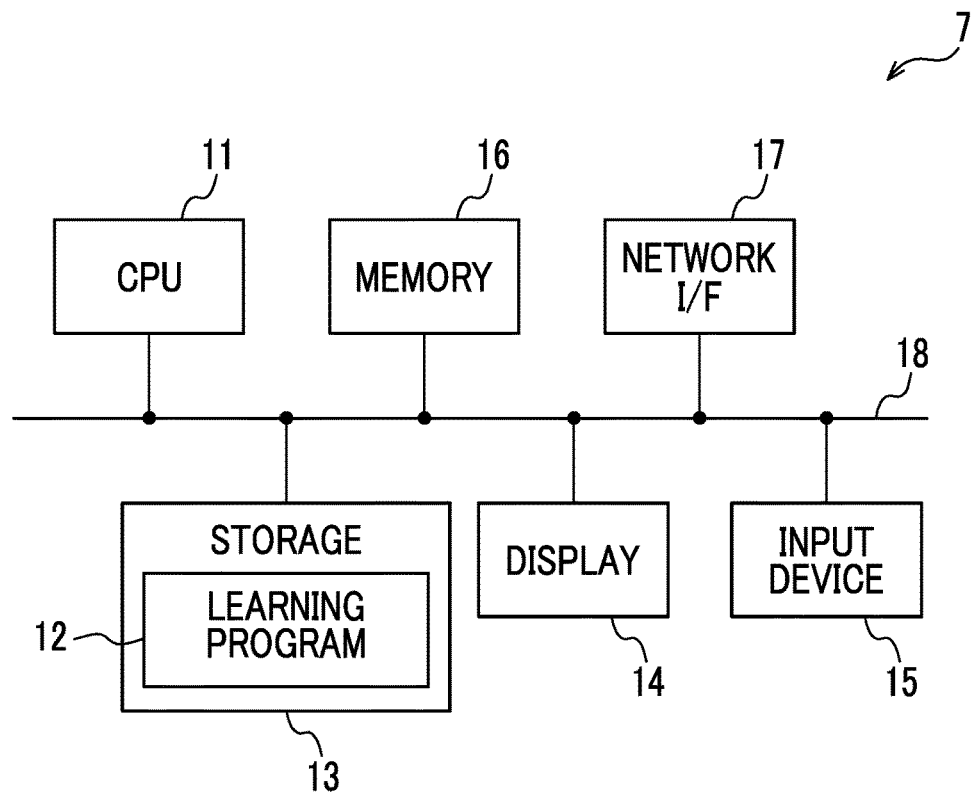
FIG. 2 is a diagram showing a schematic configuration of the learning device according to the first embodiment.

Next, the learning device 7 will be described. A hardware configuration of the learning device 7 according to the first embodiment will be described with reference to FIG. 2. As shown in FIG. 2, the learning device 7 includes a central processing unit (CPU) 11, a non-volatile storage 13, and a memory 16 as a temporary storage region. In addition, the learning device 7 includes a display 14, such as a liquid crystal display, an input device 15 consisting of a pointing device, such as the keyboard and the mouse, and a network interface (I/F) 17 connected to the network 10. The CPU 11, the storage 13, the display 14, the input device 15, the memory 16, and the network I/F 17 are connected to a bus 18. It should be noted that the CPU 11 is an example of a processor according to the present disclosure.

The storage 13 is realized by a hard disk drive (HDD), a solid state drive (SSD), and a flash memory, and the like. The storage 13 as a storage medium stores a learning program 12. The CPU 11 reads out the learning program 12 from the storage 13, develops the read-out learning program 12 in the memory 16, and executes the developed learning program 12.

Figure 3:
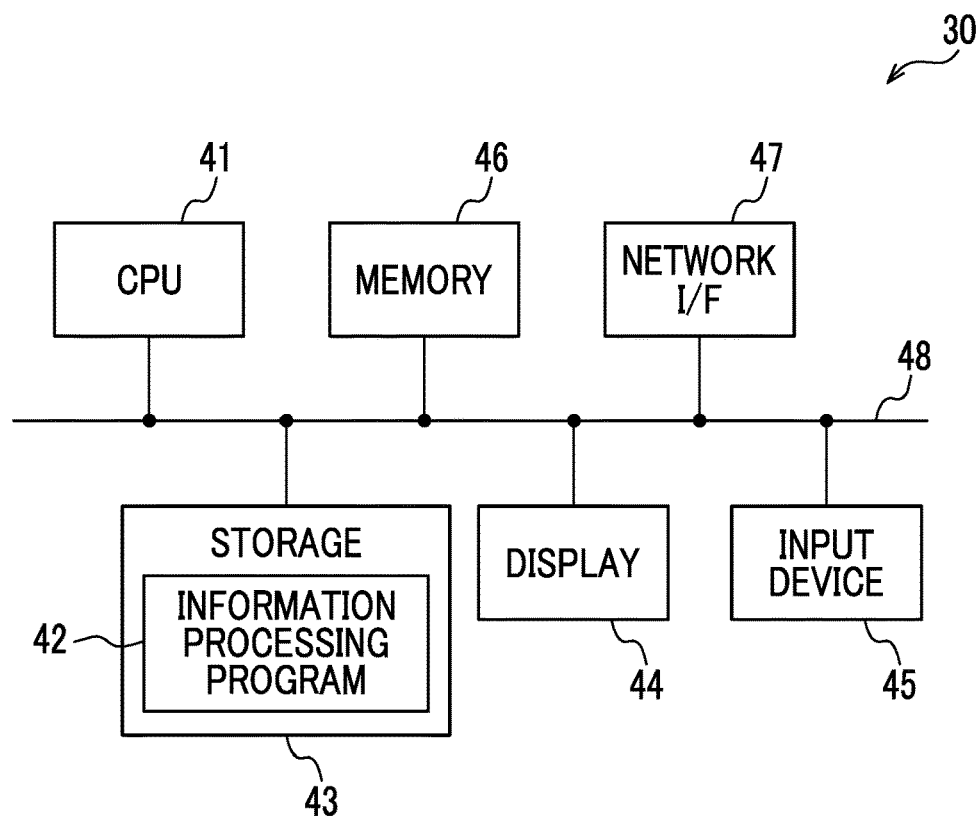
FIG. 3 is a diagram showing a schematic configuration of the information processing apparatus according to the first embodiment.

Next, an information processing apparatus 30 according to the first embodiment encompassed in the interpretation WS 3 will be described. First, a hardware configuration of the information processing apparatus 30 according to the present embodiment will be described with reference to FIG. 3. As shown in FIG. 3, the information processing apparatus 30 includes a CPU 41, a non-volatile storage 43, and a memory 46 as a temporary storage region. In addition, the information processing apparatus 30 includes a display 44, such as the liquid crystal display, an input device 45 consisting of the pointing device, such as the keyboard and the mouse, and a network I/F 47 connected to the network 10. The CPU 41, the storage 43, the display 44, the input device 45, the memory 46, and the network I/F 47 are connected to a bus 48. It should be noted that the CPU 41 is an example of the processor according to the present disclosure.

Similar to the storage 13, the storage 43 is realized by the HDD, the SSD, the flash memory, and the like. An information processing program 42 is stored in the storage 43 as the storage medium. The CPU 41 reads out the information processing program 42 from the storage 43, develops the read-out information processing program 42 in the memory 46, and executes the developed information processing program 42.

Figure 4:
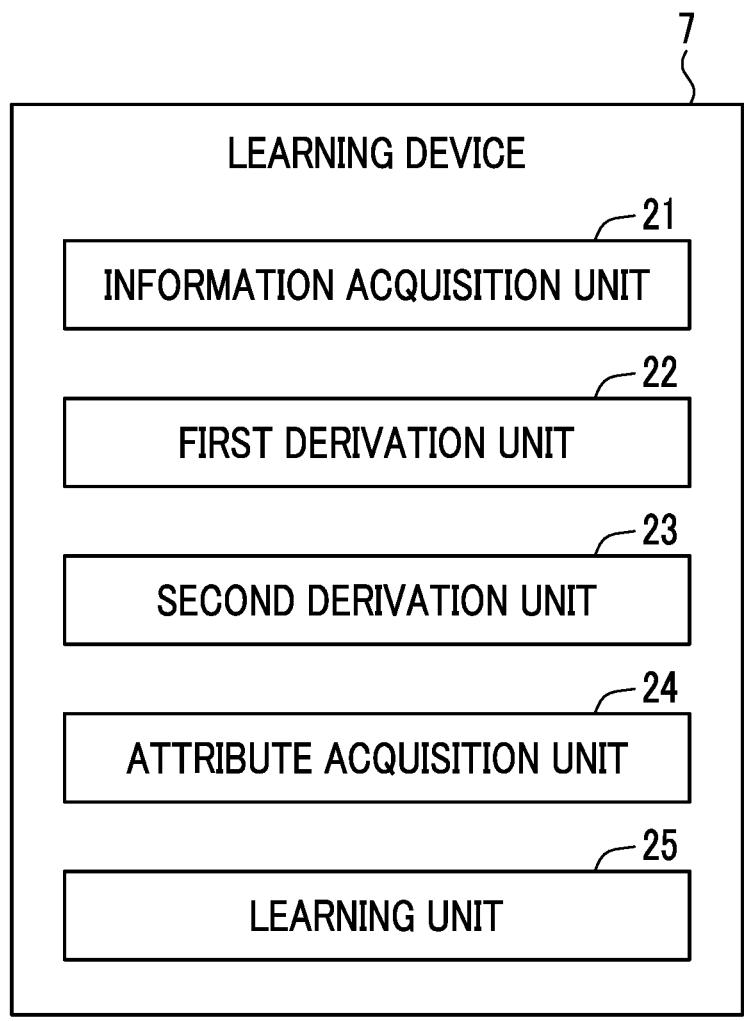
FIG. 4 is a functional configuration diagram of the learning device according to the first embodiment.

Then, a functional configuration of the learning device according to the first embodiment will be described. FIG. 4 is a diagram showing the functional configuration of the learning device according to the first embodiment. As shown in FIG. 4, the learning device 7 comprises an information acquisition unit 21, a first derivation unit 22, a second derivation unit 23, an attribute acquisition unit 24, and a learning unit 25. Moreover, by the CPU 11 executing the learning program 12, the CPU 11 functions as the information acquisition unit 21, the first derivation unit 22, the second derivation unit 23, the attribute acquisition unit 24, and the learning unit 25.

Figure 5:
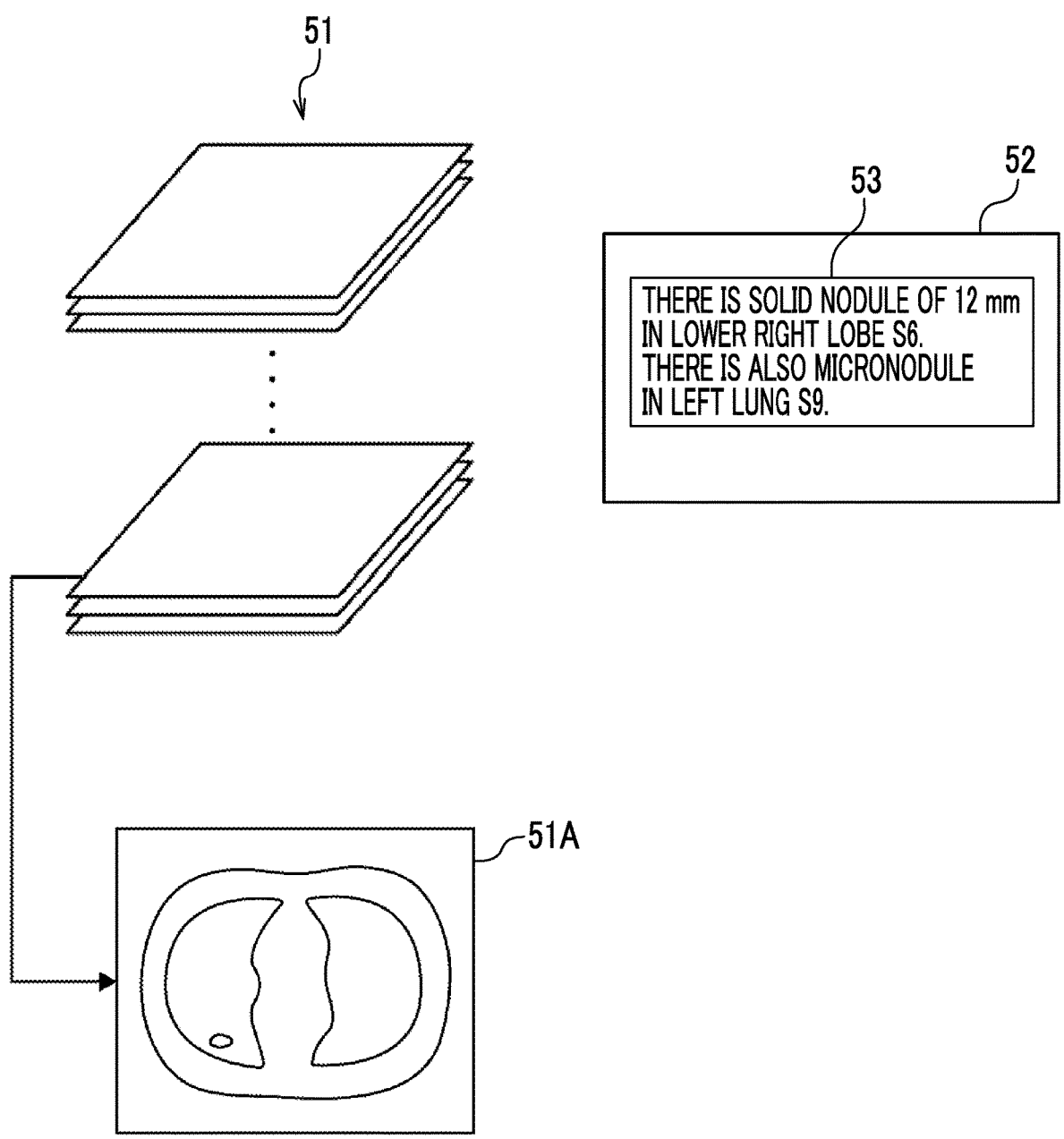
FIG. 5 is a diagram showing examples of a medical image and an interpretation report.

The information acquisition unit 21 acquires the medical image and the interpretation report from the image server 5 and the report server 6, respectively, via the network I/F 17. The medical image and the interpretation report are used to train neural networks described below. FIG. 5 is a diagram showing examples of the medical image and the interpretation report. As shown in FIG. 5, a medical image 51 is a three-dimensional image consisting of a plurality of tomographic images. In the present embodiment, the medical image 51 is a CT image of a chest of a human body. In addition, as shown in FIG. 5, the plurality of tomographic images include a tomographic image 51A including the lesion.

In addition, as shown in FIG. 5, an interpretation report 52 includes an opinion sentence 53. The description content of the opinion sentence 53 relates to, for example, the lesion included in the medical image 51, and is, for example, "There is a solid nodule of 12 mm in a lower right lobe S6. There is also a micronodule in a left lung S9."

Figure 6:
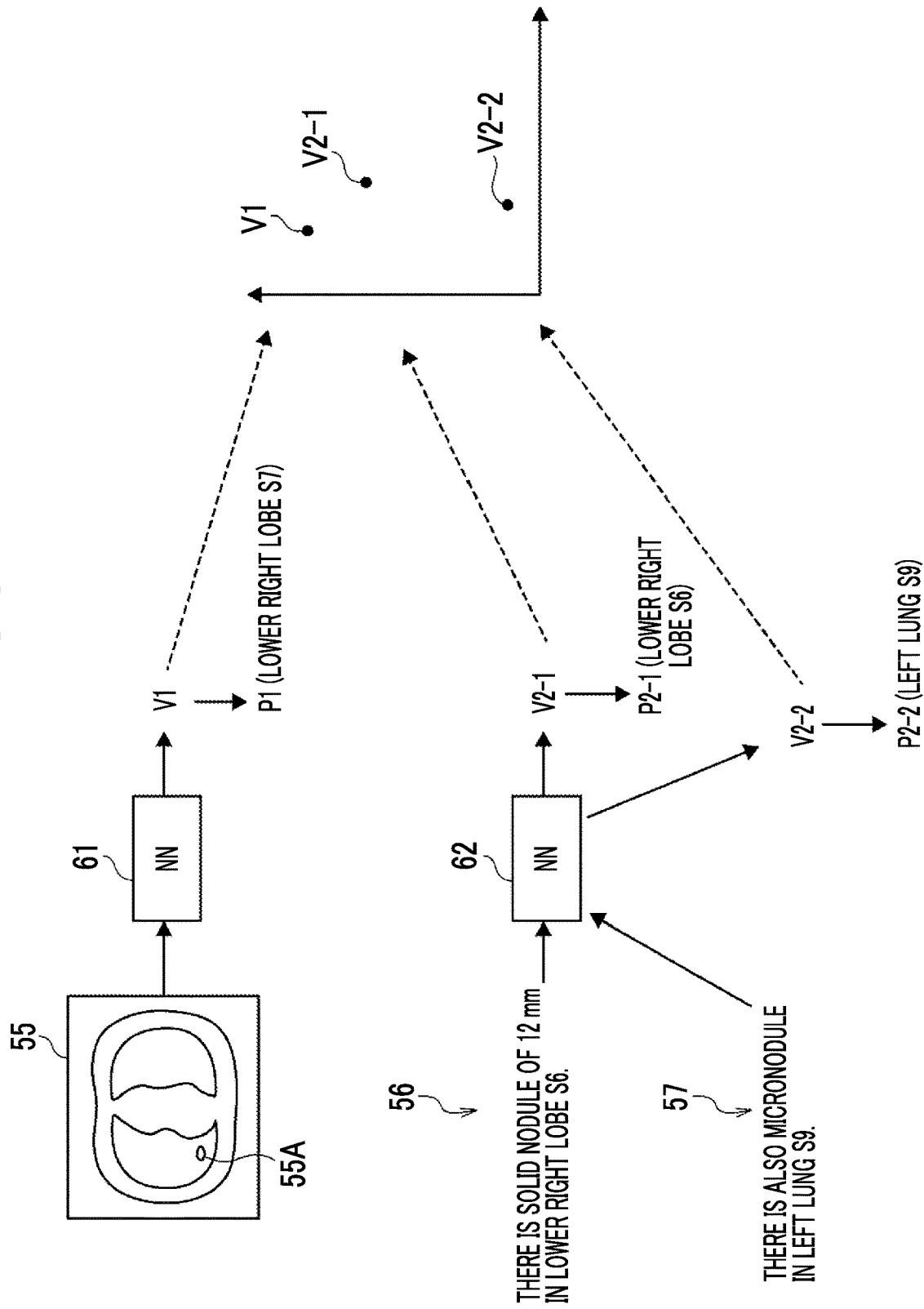
FIG. 6 is a diagram schematically showing processing performed by a first derivation unit, a second derivation unit, an attribute acquisition unit, and a learning unit in the first embodiment.

Then, the first derivation unit 22, the second derivation unit 23, the attribute acquisition unit 24, and the learning unit 25 will be described. FIG. 6 is a diagram schematically showing processing performed by the first derivation unit 22, the second derivation unit 23, the attribute acquisition unit 24, and the learning unit 25 in the first embodiment.

The first derivation unit 22 derives the first feature amount for one or more objects included in the medical image by using a first neural network (NN) 61 to construct a first derivation model that derives the feature amount for the object included in the medical image. In the present embodiment, the first neural network 61 is a convolutional neural network (CNN), but is not limited to this. As shown in FIG. 6, the first derivation unit 22 inputs an image 55, such as the medical image including the object, such as the lesion, to the first neural network 61. The first neural network 61 extracts an object 55A, such as the lesion, included in the image 55, and derives a feature vector of the object 55A as a first feature amount V1.

Figure 7:
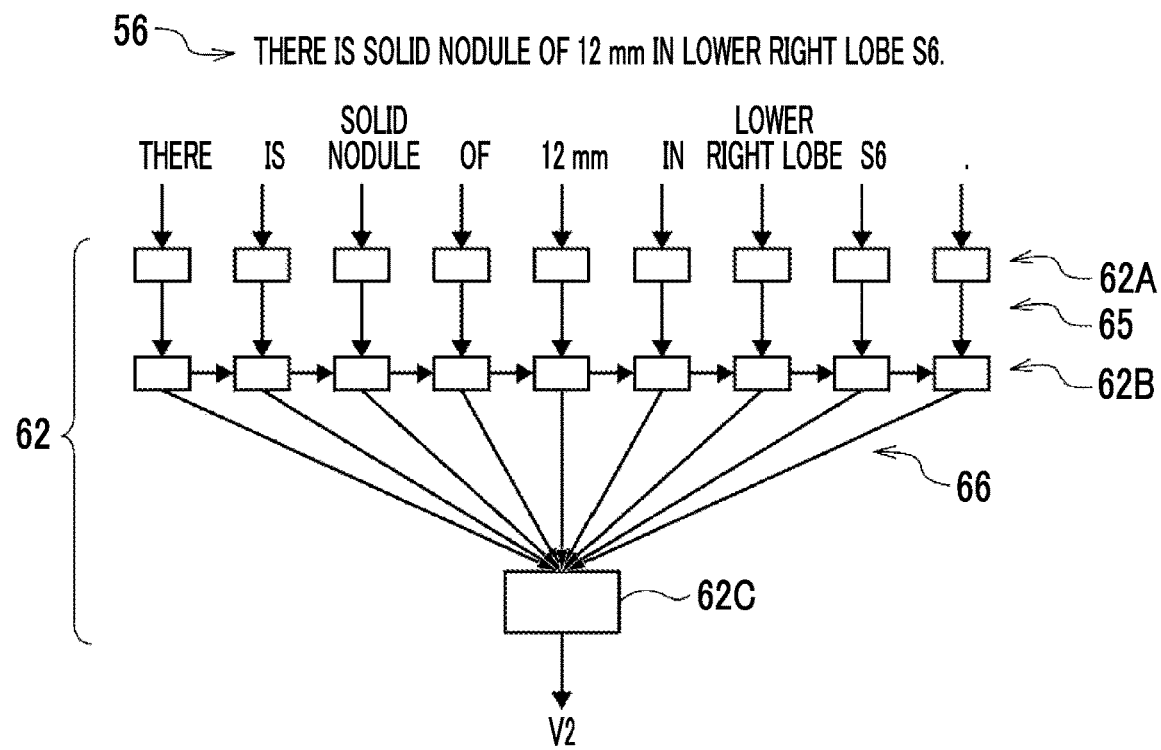
FIG. 7 is a diagram schematically showing a second neural network.

The second derivation unit 23 derives a second feature amount for a sentence including the description of the object by using a second neural network (NN) 62 to construct a second derivation model that derives the feature amount for the sentence including the description of the object. FIG. 7 is a diagram schematically showing the second neural network 62. As shown in FIG. 7, the second neural network 62 has an embedding layer 62A, a recurrent neural network layer (hereinafter, referred to as RNN layer) 62B, and a fully bonded layer 62C. The second derivation unit 23 divides the sentence into words by performing morphological analysis on the input sentence, and inputs the sentence to the embedding layer 62A. The embedding layer 62A outputs the feature vector of the word included in the input sentence. For example, in a case in which a sentence 56 describing "There is the solid nodule of 12 mm in the lower right lobe S6." is input to the second neural network 62, the sentence 56 is divided into words of "There is/solid/nodule/of/12 mm/in/lower right lobe/S6/." Moreover, each of the words is input to the element of the embedding layer 62A.

The RNN layer 62B outputs a feature vector 66 considering the context of a feature vector 65 of the words. The fully bonded layer 62C integrates the feature vector 66 output by the RNN layer 62B, and outputs the feature vector of the sentence 56 input to the second neural network 62 as a second feature amount V2. It should be noted that, in a case in which the feature vector 66 output by the RNN layer 62B is input to the fully bonded layer 62C, the weighting of the feature vector 66 for important words may be increased.

Here, in the first embodiment, a second feature amount V2-1 is acquired by the sentence 56 of "There is the solid nodule of 12 mm in the lower right lobe S6." A second feature amount V2-2 is acquired by a sentence 57 of "There is also the micronodule in the left lung S9."

The attribute acquisition unit 24 acquires a first attribute P1, which is an attribute of the object 55A included in the image 55, and second attributes P2-1 and P2-2, which are the attributes of the sentences 56 and 57, respectively. In the following, the second attributes P2-1 and P2-2 may be represented by a second attribute P2. In the first embodiment, the first attribute P1 is the position of the object 55A included in the image 55, and the second attribute P2 is the position of the object described in the sentences 56 and 57. The attribute acquisition unit 24 acquires the first attribute P1 based on one or more elements representing the position included in the first feature amount V1. In addition, the attribute acquisition unit 24 acquires the second attributes P2-1 and P2-2 based on one or more elements representing the positions included in the second feature amounts V2-1 and V2-2. In the present embodiment, the "lower right lobe S7" is acquired as the first attribute P1, the "lower right lobe S6" is acquired as the second attribute P2-1, and the "left lung S9" is acquired as the second attribute P2-2.

It should be noted that the attribute acquisition unit 24 includes a derivation model that has been subjected to machine learning to derive the attribute of the object included in the image, and a derivation model that has been subjected to machine learning to derive the attribute of the object described in the sentence. The attribute output by each derivation model includes the position of the lesion, as well as the type, the size, and the property of the lesion. It should be noted that, as the property of the object, the determination result of whether it is positive or negative for a plurality of types of property items is derived. Examples of the property items include, a shape of the margin (lobular or spicula), an absorption value (solidity or ground glass), the boundary clarity, the presence or absence of calcification, and the presence or absence of pleura invagination, for the lesion included in the lung.

The learning unit 25 trains the first neural network 61 and the second neural network 62 such that, as relevance of a combination of the first attribute P1 and the second attribute P2 is higher, a distance between the derived first feature amount V1 and second feature amount V2 in the feature space to which the first feature amount V1 and the second feature amount V2 belong is smaller than a case in which the relevance of the combination of the first attribute P1 and the second attribute P2 is low. Therefore, the learning unit 25 derives the relevance of the combination of the first attribute P1 and the second attribute P2.

Figure 8:
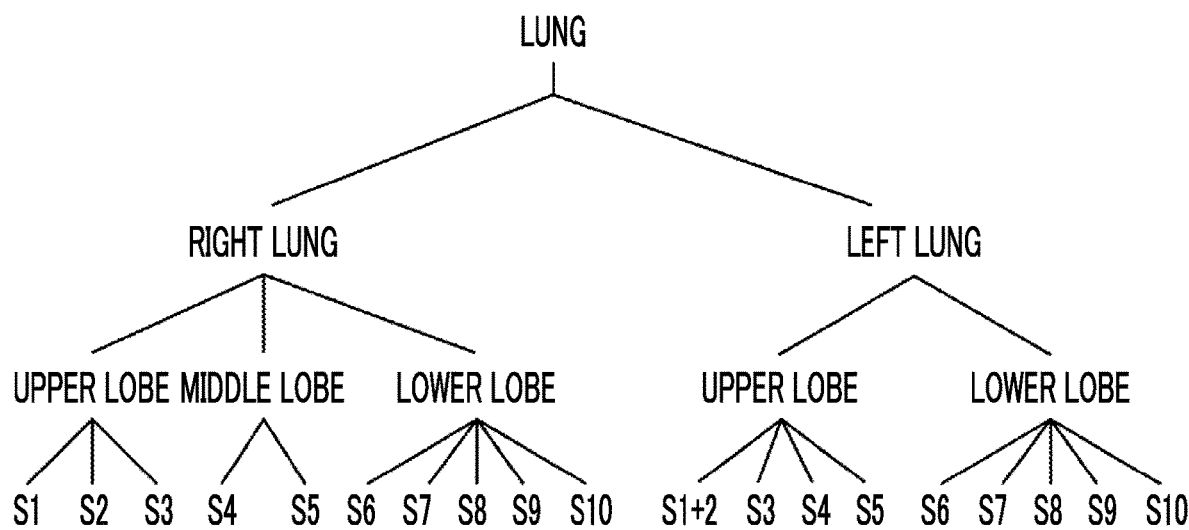
FIG. 8 is a diagram for describing relevance between positions of sections constituting a lung.

FIG. 8 is a diagram for describing the relevance between the positions of the sections constituting the lung. As shown in FIG. 8, the lung has a right lung and a left lung, the right lung is divided into an upper lobe, a middle lobe, and a lower lobe, and the left lung is divided into an upper lobe and a lower lobe. Further, a right lung upper lobe is divided into sections S1 to S3, a right lung middle lobe is divided into sections S4 and S5, and a right lung lower lobe is divided into sections S6 to S10. A left lung upper lobe is divided into sections S1+2 to S5, and a left lung lower lobe is divided into sections S6 to S10. It should be noted that the lower right lobe is synonymous with the right lung lower lobe.

The learning unit 25 determines the relevance of the combination of the first attribute Pb and the second attribute P2 based on a distance between a position represented by the first attribute P1 and a position represented by the second attribute P2. For example, in a case in which the position represented by the first attribute P1 and the position represented by the second attribute P2 are in the same lung lobe, and the sections are the same or adjacent to each other, the learning unit 25 determines that the relevance of the combination is "high". In other cases, the relevance of the combination is determined to be "low". It should be noted that the relevance of the combination is not limited to two types of "high" and "low", and three or more types of relevance may be determined. For example, in a case in which the position represented by the first attribute Pb and the position represented by the second attribute P2 are the same, the relevance of the combination may be determined to be "high", in a case in which the sections are adjacent to each other, the relevance of the combination may be determined to be "slightly high", and in other cases, the relevance of the combination may be determined to be "low".

It should be noted that the determination of the relevance of the combination may be made based on a rule, or may be performed by using a trained model that has been subjected to learning to output the relevance of the combination in a case in which the first attribute P1 and the second attribute P2 are input.

The learning unit 25 plots the first feature amount V1 and the second feature amount V2 in the feature space defined by the first feature amount V1 and the second feature amount V2. Moreover, the learning unit 25 derives the distance between the first feature amount V1 and the second feature amount V2 in the feature space. Here, since the first feature amount V1 and the second feature amount V2 are n-dimensional vectors, the feature space is also n-dimensional. It should be noted that, in FIG. 6, for the sake of description, the first feature amount V1 and the second feature amount V2 are two-dimensional, and a state in which the first feature amount V1 and the second feature amount V2 (V2-1 and V2-2) are plotted in the two-dimensional feature space is shown.

In a case in which the relevance of the combination of the first attribute P1 and the second attribute P2 is "high", the learning unit 25 trains the first neural network 61 and the second neural network 62 such that the first feature amount V1 and the second feature amount V2 get close to each other in the feature space. On the other hand, in a case in which the relevance of the combination of the first attribute P1 and the second attribute P2 is "low", the learning unit 25 trains the first neural network 61 and the second neural network 62 such that the first feature amount V1 and the second feature amount V2 are separated from each other in the feature space.

Here, since the first attribute P1 is the lower right lobe S7 and the second attribute P2-1 is the lower right lobe S6, the relevance of the combination of the first attribute P1 and the second attribute P2-1 is "high". On the other hand, since the second attribute P2-2 is the left lung S9, the relevance of the combination of the first attribute P1 and the second attribute P2-2 is "low". Therefore, in the feature space shown in FIG. 6, the learning unit 25 trains the first neural network 61 and the second neural network 62 such that the derived first feature amount V1 and second feature amount V2-1 get close to each other, and the derived first feature amount V1 and second feature amount V2-2 are separated from each other.

Figure 9:
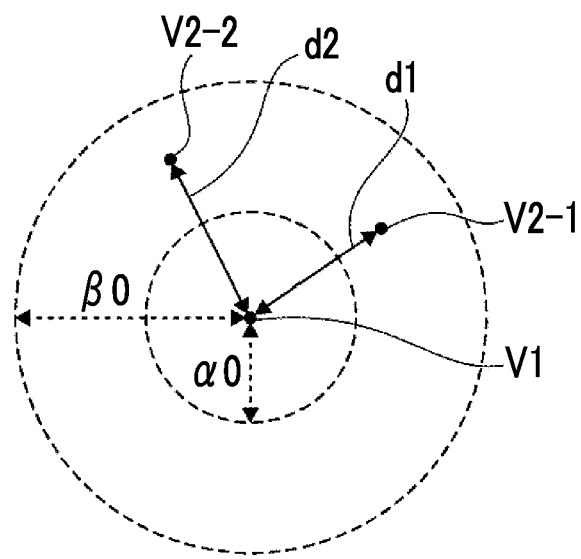
FIG. 9 is a diagram for describing the derivation of a loss.

Therefore, the learning unit 25 derives the distance between the first feature amount V1 and the second feature amount V2 in the feature space. As the distance, any distance, such as a Euclidean distance and the Mahalanobis distance, can be used. Moreover, a loss used in learning is derived based on the distance. FIG. 9 is a diagram for describing the derivation of the loss. First, the learning unit 25 calculates a distance d1 in the feature space for the first feature amount V1 and the second feature amount V2-1 of which the relevance of the combination is "high". Moreover, the distance d1 is compared with a predetermined threshold value $\alpha 0$ to derive a loss L1 based on Expression (1).

That is, in a case in which the distance d1 between the first feature amount V1 and the second feature amount V2-1 is larger than the threshold value $\alpha 0$, the loss L1, which is for training the first and second neural networks 61 and 62 such that the distance of the second feature amount V2-1 from the first feature amount V1 is smaller than the threshold value α0, is calculated by d1-α0. On the other hand, in a case in which the distance d1 between the first feature amount V1 and the second feature amount V2-1 is equal to or smaller than the threshold value α0, it is not necessary to reduce the distance d1 between the first feature amount V1 and the second feature amount V2-1, so that the loss L1 is set to 0.

$$L1 = d1 - \alpha 0 \ (d1 > \alpha 0)$$

$$L1 = 0 \ (d1 \leq \alpha 0) \quad (1)$$

On the other hand, the learning unit 25 calculates a distance d2 in the feature space for the first feature amount V1 and the second feature amount V2-2 of which the relevance between the attributes is "low". Moreover, the distance d2 is compared with a predetermined threshold value β0 to derive a loss L2 based on Expression (2).

That is, in a case in which the distance d2 between the first feature amount V1 and the second feature amount V2-2 is smaller than the threshold value β0, the loss L2, which is for training the first and second neural networks 61 and 62 such that the distance of the second feature amount V2-2 from the first feature amount V1 is larger than the threshold value β0, is calculated by β0-d2. On the other hand, in a case in which the distance d2 between the first feature amount V1 and the second feature amount V2-2 is equal to or larger than the threshold value β0, it is not necessary to increase the distance d2 between the first feature amount V1 and the second feature amount V2-2, so that the loss L2 is set to 0.

$$L2 = \beta 0 - d2 \ (d2 < \beta 0)$$

$$L2 = 0 \ (d2 \geq \beta 0) \quad (2)$$

The learning unit 25 trains the first neural network 61 and the second neural network 62 based on the derived losses L1 and L2. That is, in a case of d1>α0 and in a case of d2<β0, a kernel coefficient used in the weights and convolutions of the bonding between the layers constituting each of the first neural network 61 and the second neural network 62 is learned such that the losses L1 and L2 are reduced.

Moreover, the learning unit 25 repeatedly performs learning until the loss L1 is equal to or smaller than the predetermined threshold value α0 and the loss L2 is equal to or larger than the threshold value β0. It should be noted that it is preferable that the learning unit 25 repeatedly perform learning until the loss L1 is continuously equal to or smaller than the threshold value α0 a predetermined number of times and the loss L2 is continuously equal to or larger than the threshold value β0 a predetermined number of times. As a result, the first derivation model that derives the first feature amount V1 and the second derivation model that derives the second feature amount V2 are constructed such that the distance in the feature space is reduced in a case in which the relevance of the combination of the attribute of the object included in the image and the attribute of the object described in the sentence is high and the distance in the feature space is increased in a case in which the relevance of the combination is low. It should be noted that the learning unit 25 may repeatedly perform learning a predetermined number of times.

The first derivation model and the second derivation model constructed in this way are transmitted to the interpretation WS 3 and used in the information processing apparatus according to the first embodiment.

It should be noted that, in the first embodiment, even in a case in which the medical image and the interpretation report acquired by the information acquisition unit 21 are associated with each other, that is, the opinion sentence included in the interpretation report relates to the opinion of the medical image, the relationship thereof is not taken into consideration in a case of learning described below, and the first and second neural networks 61 and 62 learn only based on the relevance of the combination of the first attribute P1 and the second attribute P2.

Figure 10:
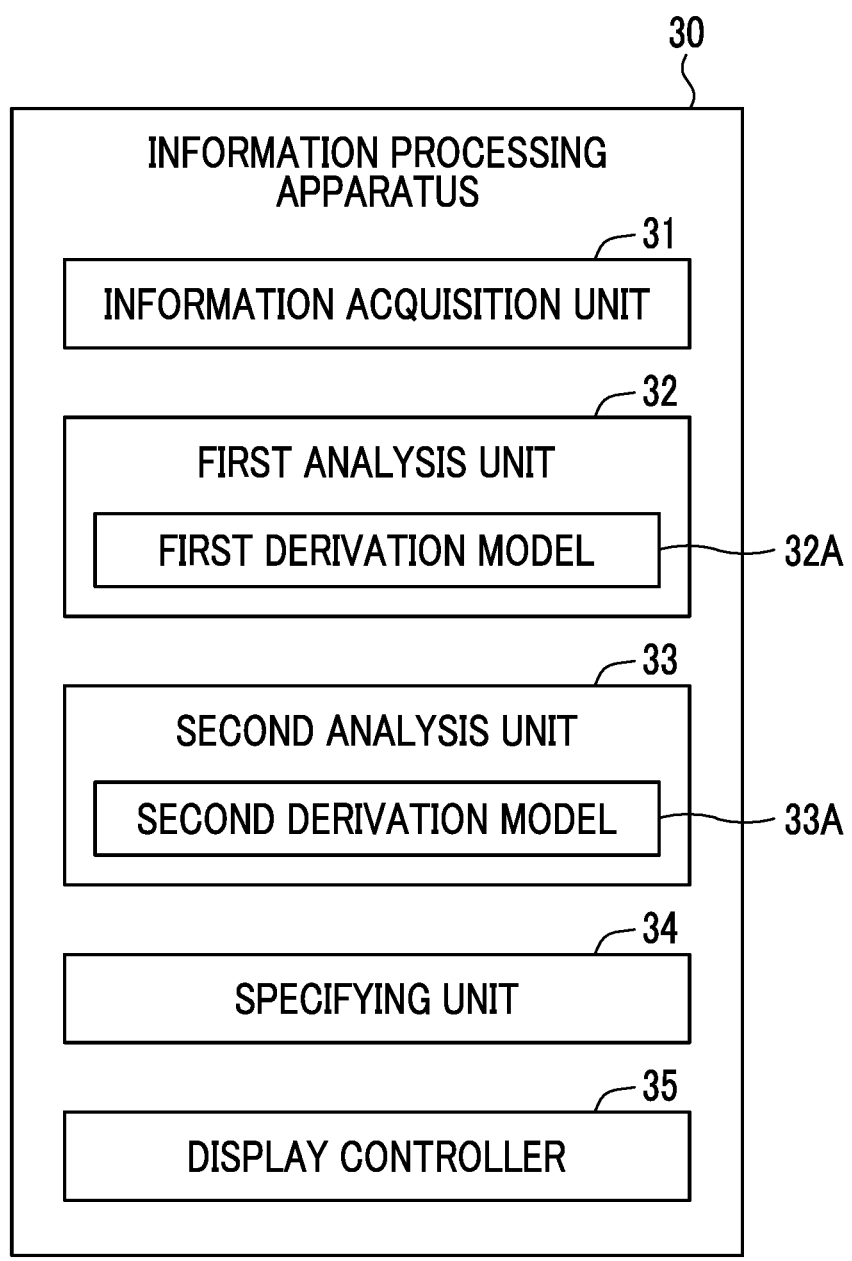
FIG. 10 is a functional configuration diagram of the information processing apparatus according to the first embodiment.

Then, a functional configuration of the information processing apparatus according to the first embodiment will be described. FIG. 10 is a diagram showing the functional configuration of the information processing apparatus according to the first embodiment. As shown in FIG. 10, the information processing apparatus 30 comprises an information acquisition unit 31, a first analysis unit 32, a second analysis unit 33, a specifying unit 34, and a display controller 35. Moreover, by the CPU 41 executing the information processing program 42, the CPU 41 functions as the information acquisition unit 31, the first analysis unit 32, the second analysis unit 33, the specifying unit 34, and the display controller 35.

The information acquisition unit 31 acquires a target medical image G0, which is the interpretation target, from the image server 5 in response to an instruction from the input device 45 by the interpreter who is an operator.

The first analysis unit 32 analyzes the target medical image G0 using a first derivation model 32A constructed by the learning device 7 described above to derive the first feature amount V1 for the object, such as the lesion, included in the target medical image G0. In the present embodiment, the target medical image G0 includes two objects, and the first feature amounts V1-1 and V1-2 are derived for each of the two objects.

Here, in the information processing apparatus 30 according to the first embodiment, the interpretation report is generated by the interpreter interpreting the target medical image G0 in the interpretation WS 3 and inputting the opinion sentence including an interpretation result by using the input device 45. The second analysis unit 33 derives the second feature amount V2 for the input opinion sentence by analyzing the input opinion sentence using a second derivation model 33A constructed by the learning device 7 described above.

Figure 11:
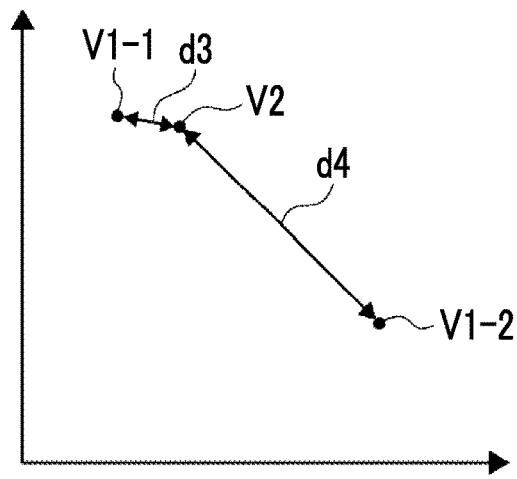
FIG. 11 is a diagram for describing specifying of a first feature amount.

The specifying unit 34 derives the distance between the first feature amount V1 derived by the first analysis unit 32 and the second feature amount V2 derived by the second analysis unit 33 in the feature space. Moreover, the first feature amount V1 corresponding to the second feature amount V2 is specified based on the derived distance. FIG. 11 is a diagram for describing specifying of the first feature amount. It should be noted that, in FIG. 11, the feature space is shown in two dimensions for the sake of description. As shown in FIG. 11, in a case in which a distance d3 between the first feature amount V1-1 and the second feature amount V2 is compared with a distance d4 between the first feature amount V1-2 and the second feature amount V2 in the feature space, d3<d4. Therefore, the specifying unit 34 specifies the first feature amount corresponding to the second feature amount V2 as the first feature amount V1-1.

Figure 12:
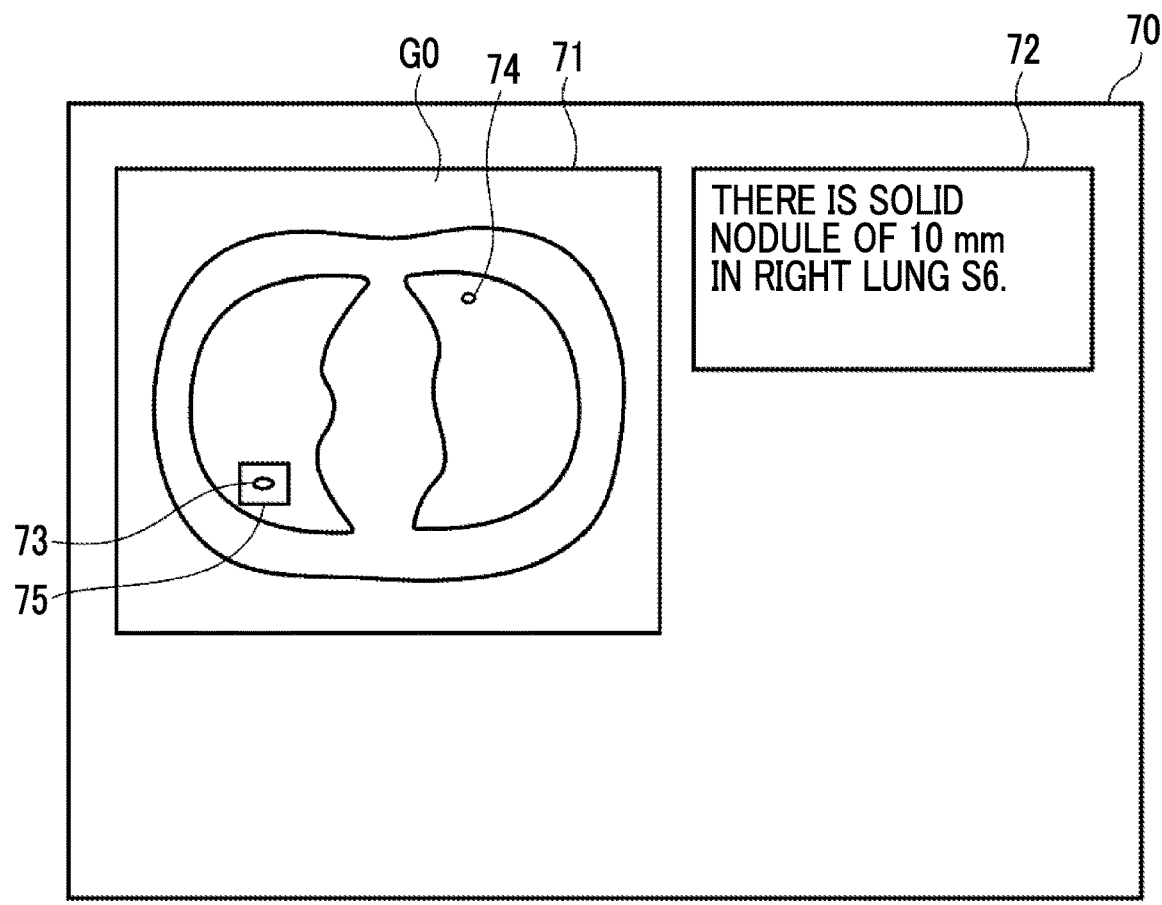
FIG. 12 is a diagram showing a display screen.

The display controller 35 displays the object from which the specified first feature amount is derived, in distinction from other regions in the target medical image G0. FIG. 12 is a diagram showing a creation screen of the interpretation report displayed on the interpretation WS 3. As shown in FIG. 12, a creation screen 70 of the interpretation report includes an image display region 71 and a sentence display region 72. The target medical image G0 is displayed in the image display region 71. In FIG. 12, the target medical image G0 is one tomographic image constituting a three-dimensional image of the chest. The opinion sentence input by the interpreter is displayed in the sentence display region 72. In FIG. 12, the opinion sentence of "There is a solid nodule of 10 mm in a right lung S6." is displayed. It should be noted that the right lung S6 is synonymous with the right lung lower lobe S6.

The target medical image G0 shown in FIG. 12 includes a lesion 73 in the right lung and a lesion 74 in the left lung. In a case in which the first feature amount V1-1 derived for the lesion 73 of the right lung is compared with the first feature amount V1-2 derived for the lesion 74 of the left lung, the distance from the second feature amount V2 derived for the opinion sentence of "There is the solid nodule of 10 mm in the right lung S6." is smaller in the first feature amount V1-1. Therefore, the display controller 35 displays the lesion 73 of the right lung in distinction from other regions in the target medical image G0. In FIG. 12, by surrounding the lesion 73 of the right lung by a rectangular mark 75, the lesion 73 is displayed in distinction from other regions, but the present disclosure is not limited to this. A mark of any shape, such as an arrow, can be used.

Figure 13:
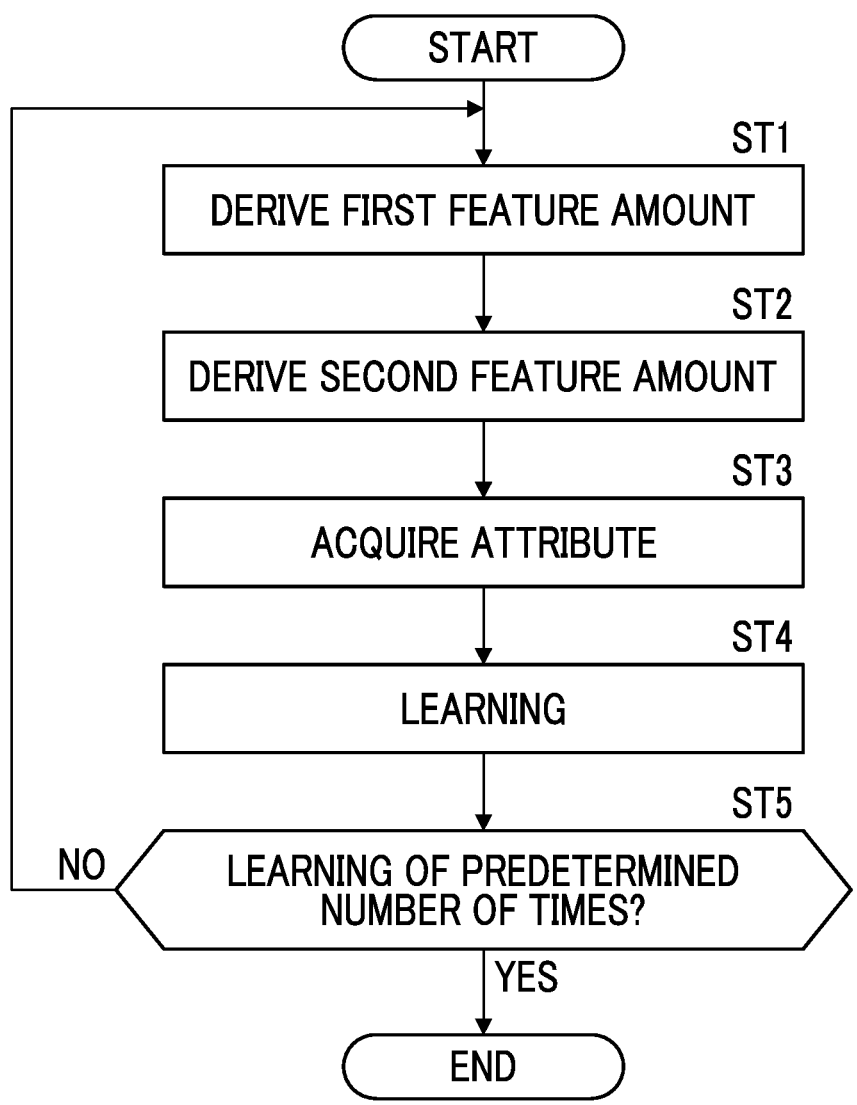
FIG. 13 is a flowchart showing learning processing performed in the first embodiment.

Then, processing performed in the first embodiment will be described. FIG. 13 is a flowchart of learning processing according to the first embodiment. It should be noted that, the image and the interpretation report used in learning are acquired from the image server 5 and the report server 6 by the information acquisition unit 21, respectively, and stored in the storage 13. In addition, a learning end condition is that learning is performed a predetermined number of times.

First, the first derivation unit 22 derives the first feature amount V1 for the object included in the image by the first neural network 61 (step ST1). In addition, the second derivation unit 23 derives the second feature amount V2 for the sentence including the description of the object by the second neural network 62 (step ST2). It should be noted that the processing of step ST2 may be performed first, or the processing of step ST1 and step ST2 may be performed in parallel.

Then, the attribute acquisition unit 24 acquires the first attribute P1, which is the attribute of the object included in the image, and the second attribute P2, which is the attribute of the sentence (attribute acquisition: step ST3). Moreover, the learning unit 25 trains the first neural network and the second neural network such that the distance between the derived first feature amount V1 and second feature amount V2 is smaller as the relevance of the combination of the first attribute P1 and the second attribute P2 is higher (step ST4). Further, the learning unit 25 determines whether or not learning has been performed a predetermined number of times (learning of a predetermined number of times: step ST5), and in a case in which a negative determination is made in step ST5, the learning unit 25 returns to step ST1 and repeats the processing of step ST1 to step ST5. In a case in which a positive determination is made in step ST5, the processing ends.

Then, information processing according to the first embodiment will be described. FIG. 14 is a flowchart of the information processing according to the first embodiment. It should be noted that, the target medical image G0, which is a processing target, is acquired by the information acquisition unit 31 and stored in the storage 43. First, the first analysis unit 32 analyzes the target medical image G0 using the first derivation model 32A to derive the first feature amount V1 for the object, such as the lesion, included in the target medical image G0 (step ST11).

Then, the information acquisition unit 31 acquires the opinion sentence input by the interpreter using the input device 45 (step ST12), and the second analysis unit 33 analyzes the input opinion sentence using the second derivation model 33A to derive the second feature amount V2 for the input opinion sentence (step ST13).

Subsequently, the specifying unit 34 derives the distance between the first feature amount V1 derived by the first analysis unit 32 and the second feature amount V2 derived by the second analysis unit 33 in the feature space, and specifies the first feature amount V1 corresponding to the second feature amount V2 based on the derived distance (step ST14). Moreover, the display controller 35 displays the object from which the specified first feature amount V1 is derived, in distinction from other regions in the target medical image G0 (step ST15), and the processing ends.

As described above, in the learning device according to the first embodiment, the first derivation model 32A and the second derivation model 33A are constructed by training the first neural network 61 and the second neural network 62 such that the distance between the derived first feature amount V1 and second feature amount V2 in the feature space to which the first feature amount V1 and the second feature amount V2 belong is smaller as the relevance of the combination of the first attribute P1 and the second attribute P2 is higher.

Therefore, by applying the first derivation model 32A and the second derivation model 33A constructed by learning to the information processing apparatus 30 according to the first embodiment, the first feature amount V1 and the second feature amount V2 are derived such that the medical image including the object having high relevance of the combination of the attributes and the sentence including the description of the object are associated with each other, and the medical image including the object having low relevance of the combination of the attributes and the sentence including the description of the object are not associated with each other. Therefore, by using the derived first feature amount V1 and second feature amount V2 it is possible to accurately associate the image with the sentence.

In addition, since it is possible to accurately associate the image with the sentence, it is possible to accurately specify the object described in the input opinion sentence in the medical image in a case of creating the interpretation report for the medical image.

It should be noted that, in the learning device according to the first embodiment, the attribute acquisition unit 24 acquires the position of the object as the first attribute P1 and the second attribute P2, but the present disclosure is not limited to this. The property of the object included in the image may be acquired as the first attribute P1, and the property of the object described in the sentence may be acquired as the second attribute P2. In the following, this case will be described as a second embodiment. It should be noted that, since a configuration of the learning device according to the second embodiment is the same as the configuration of the learning device according to the first embodiment and only the processing to be performed is different, the description of the configuration of the device will be omitted.

In the second embodiment, the learning unit 25 of the learning device 7 determines the relevance of the combination of the first attribute P1 and the second attribute P2 based on a co-occurrence relationship of a text representing the property. Here, the co-occurrence means that a certain character string and a certain character string appear at the same time in any document or sentence in the field of natural language processing. For example, a word of "irregular shape" is often described in the opinion sentence along with a word of "serration", but is rarely described in the opinion sentence along with a word of "oval shape". Therefore, the "irregular shape" and the "serration" co-occur more, and the "irregular shape" and the "oval shape" rarely co-occur.

In the second embodiment, the co-occurrence relationship of words included in a plurality of opinion sentences is derived in advance and stored in the storage 43. The co-occurrence relationship may be derived by a manual operation, or may be derived by analyzing the plurality of opinion sentences. In this case, the co-occurrence relationship may be derived from the opinion sentence by using a trained model that has been subjected to learning, or the co-occurrence relationship may be derived based on a rule.

FIG. 15 is a diagram showing an example of the co-occurrence relationship. It should be noted that, in FIG. 15, the magnitude of the co-occurrence relationship is shown by a numerical value equal to or larger than 0 and equal to or smaller than 1. As shown in FIG. 15, the co-occurrence relationship between the "irregular shape" and the "serration" is 0.96, and the co-occurrence relationship between the "irregular shape" and the "oval shape" is 0.10.

In the second embodiment, the attribute acquisition unit 24 acquires the property of the object 55A included in the image 55 as the first attribute P1, and acquires the property of the object described in the sentence 56 as the second attribute P2. Moreover, in the second embodiment, the learning unit 25 trains the first and second neural networks 61 and 62 such that the distance between the first feature amount V1 and the second feature amount V2 in the feature space is smaller as the relevance of the combination of the first attribute P1 and the second attribute P2, which are properties of the objects, is higher.

Figure 16:
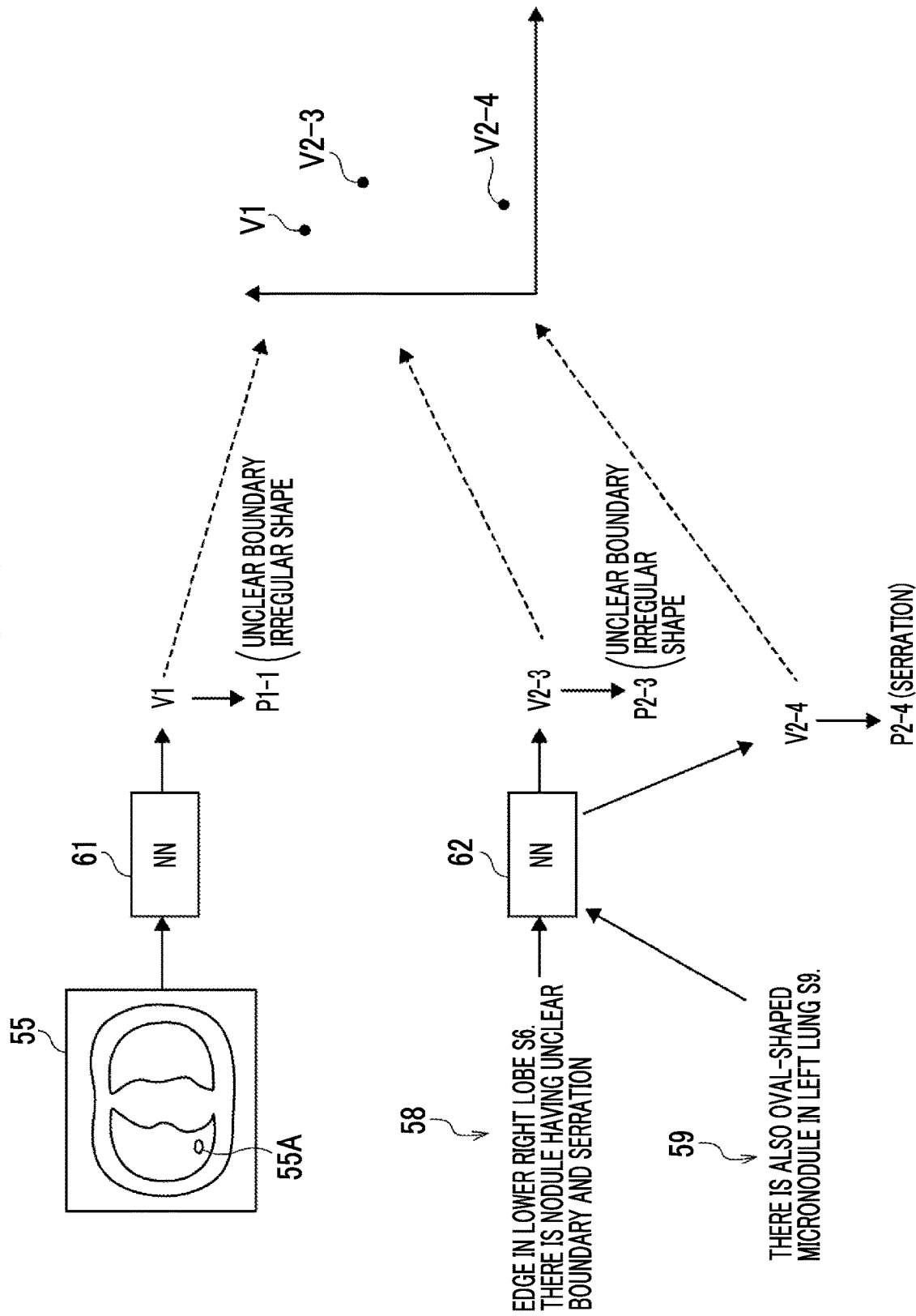
FIG. 16 is a diagram schematically showing processing performed by a first derivation unit, a second derivation unit, an attribute acquisition unit, and a learning unit in a second embodiment.

FIG. 16 is a diagram schematically showing processing performed by the first derivation unit 22, the second derivation unit 23, the attribute acquisition unit 24, and the learning unit 25 in the second embodiment. It should be noted that, in FIG. 16, the same configurations as those in FIG. 6 are denoted by the same reference numerals, and the detailed description thereof will be omitted. In the second embodiment, the same image 55 as in the first embodiment is used in learning of the first neural network 61. On the other hand, in learning of the second neural network 62, a sentence 58 of "There is a nodule having an unclear boundary and a serration edge in the lower right lobe S6." and a sentence 59 of "There is also an oval-shaped micronodule in the left lung S9." are used.

In the second embodiment, the first derivation unit 22 extracts the object 55A, such as the lesion, included in the image 55, by the first neural network 61 as in the first embodiment, and derives the feature amount of the object 55A as the first feature amount V1.

The second derivation unit 23 derives the feature amounts for the sentences 58 and 59 as second feature amounts V2-3 and V2-4 by the second neural network 62.

In the second embodiment, the attribute acquisition unit 24 acquires the property of the object 55A included in the image 55 as the first attribute P1-1, and acquires the properties of the objects described in the sentences 58 and 59 as second attributes P2-3 and P2-4. In the second embodiment, the "unclear boundary" and the "irregular shape" are acquired as the first attribute P1-1, the "unclear boundary" and the "serration" are acquired as the second attribute P2-3, and the "oval shape" is acquired as the second attribute P2-4.

In the second embodiment, the learning unit 25 derives the relevance of the combination of the first attribute P1-1, and the second attributes P2-3 and P2-4 based on the co-occurrence relationship. Here, in the second embodiment, the first attribute P1-1 is the "unclear boundary" and the "irregular shape", and the second attribute P2-3 is the "unclear boundary" and the "serration". The first attribute P1-1 and the second attribute P2-3 have the common "unclear boundary" property. In a case in which a plurality of properties are included as the attributes, the learning unit 25 derives the relevance of the combination by using different properties other than the common property. Therefore, in a case of deriving the relevance of the combination of the first attribute P1-1 and the second attribute P2-3, the learning unit 25 derives the relevance of the combination of the "irregular shape" and the "serration". Here, as shown in FIG. 15, the co-occurrence relationship between the "irregular shape" and the "serration" is 0.96.

On the other hand, in a case of deriving the relevance of the combination of the first attribute P1-1 and the second attribute P2-4, the learning unit 25 derives the relevance of the combination based on a smaller co-occurrence relationship between the co-occurrence relationship between the "unclear boundary" and the "oval shape" and the co-occurrence relationship between the "irregular shape" and the "oval shape". As shown in FIG. 15, a value of the co-occurrence relationship between the "irregular shape" and the "oval shape" is 0.10, and for example, a value of the co-occurrence relationship between the "unclear boundary" and the "oval shape" is 0.30. In this case, the learning unit 25 derives the relevance of the combination of the first attribute P1-1 and the second attribute P2-4 based on 0.10, which is the value of the co-occurrence relationship between the "irregular shape" and the "oval shape". It should be noted that the learning unit 25 may derive the relevance of the combination based on a larger co-occurrence relationship between the co-occurrence relationship between the "unclear boundary" and the "oval shape" and the co-occurrence relationship between the "irregular shape" and the "oval shape". In addition, the learning unit 25 may derive the relevance of the combination based on an average of the values the co-occurrence relationship between the "unclear boundary" and the "oval shape" and the co-occurrence relationship between the "irregular shape" and the "oval shape".

In the second embodiment, the learning unit 25 determines that the relevance of the combination of the first attribute P1 and the second attribute P2 is "high" in a case in which the co-occurrence relationship is equal to or higher than a predetermined threshold value. In a case in which the co-occurrence relationship is lower than the threshold value, the relevance of the combination of the first attribute P1 and the second attribute P2 is determined to be "low". For example, 0.7 can be used as the threshold value. Therefore, the learning unit 25 determines that the relevance of the combination of the first attribute P1-1 and the second attribute P2-3 is "high", and determines that the relevance of the combination of the first attribute P1-1 and the second attribute P2-4 is "low".

It should be noted that the relevance is not limited to two types of "high" and "low", and three or more types of relevance may be determined. For example, the relevance may be determined to be "high", "slightly high", and "low" in accordance with the position represented by the first attribute P1 and the value of the co-occurrence relationship represented by the second attribute P2.

In the second embodiment, the learning unit 25 plots the first feature amount V1 and the second feature amounts V2-3 and V2-4 in the feature space. Moreover, in a case in which the relevance of the combination of the first attribute P1 and the second attribute P2 is "high", the learning unit 25 trains the first neural network 61 and the second neural network 62 such that the first feature amount V1 and the second feature amount V2 get close to each other in the feature space. On the other hand, in a case in which the relevance of the combination of the first attribute P1 and the second attribute P2 is "low", the learning unit 25 trains the first neural network 61 and the second neural network 62 such that the first feature amount V1 and the second feature amount V2 are separated from each other in the feature space.

Here, the relevance of the combination of the first attribute P1-1 and the second attribute P2-3 is "high". On the other hand, the relevance of the combination of the first attribute P1 and the second attribute P2-4 is "low". Therefore, in the feature space shown in FIG. 16, the learning unit 25 trains the first neural network 61 and the second neural network 62 such that the first feature amount V1 and the second feature amount V2-3 get close to each other, and the first feature amount V1 and the second feature amount V2-4 are separated from each other. Since the derivation of the loss used in learning is the same as that of the first embodiment, the detailed description thereof will be omitted here.

It should be noted that, in the first and second embodiments, the first and second neural networks 61 and 62 learn based on the relevance of the combination of the first attribute P1 and the second attribute P2, but the present disclosure is not limited to this. In addition to the relevance of a combination of the first attribute P1 and the second attribute P2, the combination of the medical image and the interpretation report corresponding to the medical image may be used as teacher data to train the first and second neural networks 61 and 62. In the following, this case will be described as a third embodiment.

Figure 17:
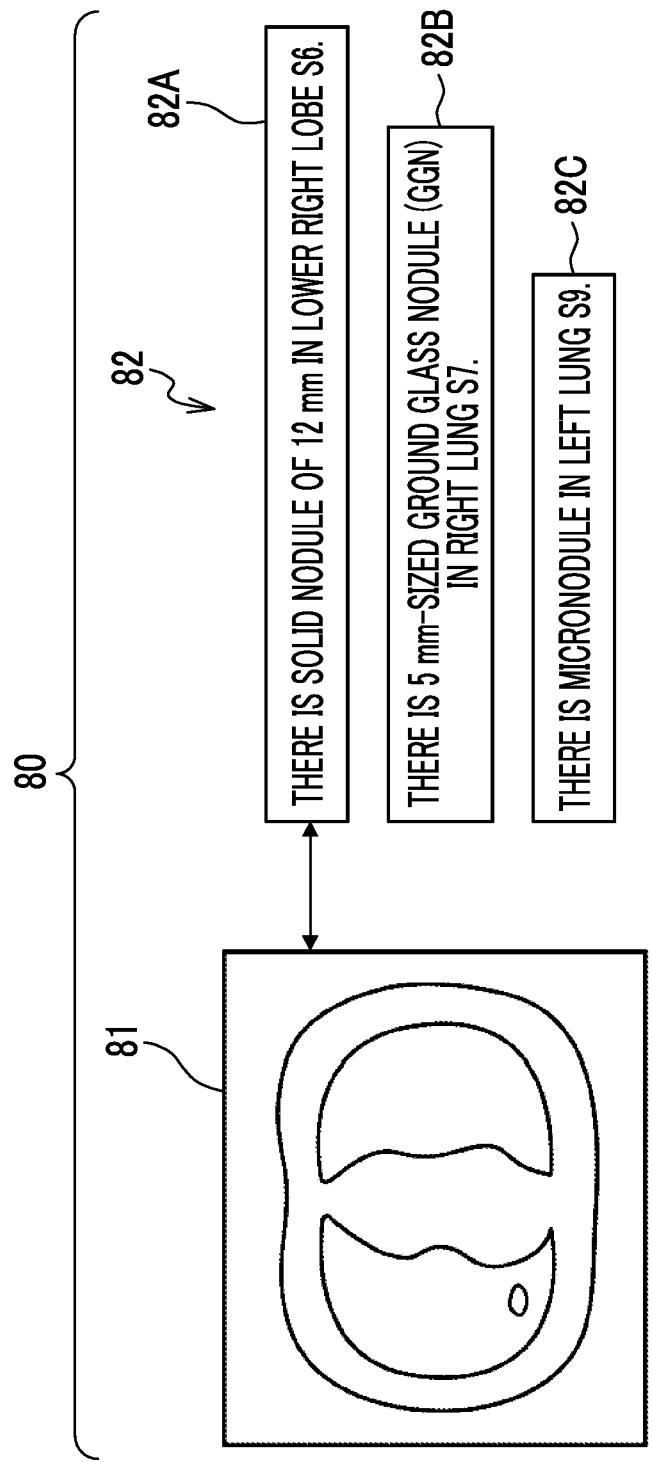
FIG. 17 is a diagram showing teacher data.

In the third embodiment, the combination of the medical image and the interpretation report corresponding to the medical image is used as the teacher data to train the first and second neural networks 61 and 62. FIG. 17 is a diagram showing the teacher data used in the third embodiment. As shown in FIG. 17, teacher data 80 consists of a teacher image 81 and an interpretation report 82 corresponding to the teacher image 81 to include the opinion sentence about the teacher image 81. The teacher image 81 is a tomographic image of the lung, and includes the lesion in the lower right lobe S6 as the object.

The interpretation report 82 includes three opinion sentences 82A to 82C. The opinion sentence 82A is "There is a solid nodule of 12 mm in the lower right lobe S6." The opinion sentence 82B is "There is a 5 mm-sized ground glass nodule (GGN) in the right lung S7." The opinion sentence 82C is "There is a micronodule in the left lung S9." Here, since the teacher image 81 includes the object in the lower right lobe S6, the opinion sentence 82A among the three opinion sentences 82A to 82C corresponds to the teacher image 81. It should be noted that the teacher image 81 is one tomographic image of the plurality of tomographic images constituting the three-dimensional image. The opinion sentences 82B and 82C are generated as a result of interpreting the tomographic images other than the teacher image 81. Therefore, the teacher image 81 and the opinion sentences 82B and 82C do not correspond to each other.

In the third embodiment, the first derivation unit 22 derives the feature amount of the teacher image 81 as a first feature amount V1-3 by the first neural network 61. In addition, the second derivation unit 23 derives the feature amounts of the opinion sentences 82A to 82C as second feature amounts V2-5, V2-6, and V2-7 by the second neural network 62.

Moreover, in the third embodiment, the attribute acquisition unit 24 acquires the attribute of the object included in the teacher image 81 as the first attribute P1-3. In addition, the attributes of the objects described in the opinion sentences 82A to 82C are acquired as the second attributes P2-5, P2-6, and P2-7. It should be noted that, in the third embodiment, the first attribute P1-3 is the position of the object included in the teacher image 81, and the second attributes P2-5, P2-6, and P2-7 are the positions of the objects described in the opinion sentences 82A to 82C. Therefore, the first attribute P1-3 is the "lower right lobe S6", the second attribute P2-5 is the "lower right lobe S6", the second attribute P2-6 is the "right lung S7", and the second attribute P2-7 is the "left lung S9". It should be noted that the first attribute P1-3 may be the property of the object included in the teacher image 81, and the second attributes P2-5, P2-6, and P2-7 may be the properties of the objects described in the opinion sentences 82A to 82C.

Figure 18:
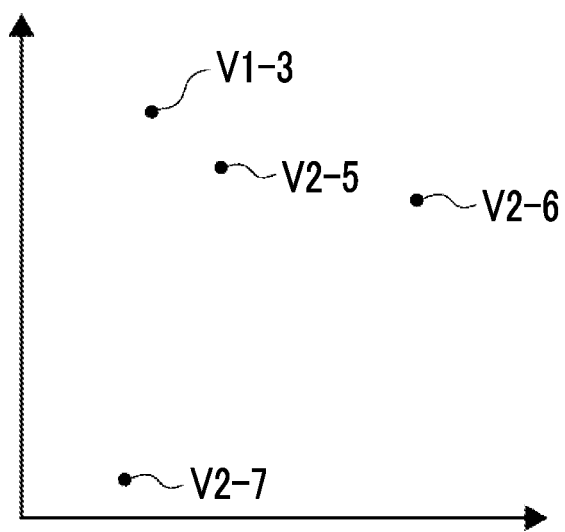
FIG. 18 is a diagram for describing a plot of a feature amount in a third embodiment.

The learning unit 25 plots the first feature amount V1-3, and the second feature amounts V2-5, V2-6, and V2-7 in the feature space. FIG. 18 is a diagram for describing the plot of the feature amount in the third embodiment. It should be noted that, also in FIG. 18, the feature space is shown in two dimensions for the sake of description. Moreover, as in the first and second embodiments, the learning unit 25 trains the first and second neural networks 61 and 62 such that the distance between the first feature amount and the second feature amount in the feature space is smaller as the relevance of the combination of the first attribute P1 and the second attribute P2 is higher.

In the third embodiment, the first attribute P1-3 is the "lower right lobe S6", the second attribute P2-5 is the "lower right lobe S6", the second attribute P2-6 is the "right lung S7", and the second attribute P2-7 is the "left lung S9". Therefore, the relevance between the first attribute P1-3 and the second attribute P2-5 is high, and the relevance between the first attribute P1-3 and the second attribute P2-6, P2-7 is low.

Therefore, the learning unit 25 trains the first neural network 61 and the second neural network 62 such that, in the feature space, the first feature amount V1-3 and the second feature amount V2-5 get close to each other, and the first feature amount V1-3 and the second feature amounts V2-6 and V2-7 are separated from each other.

Further, in the third embodiment, the first and second neural networks 61 and 62 learn based on a correspondence relationship between the teacher image 81 and the opinion sentence in the teacher data 80. That is, the learning unit 25 further trains the first and second neural networks 61 and 62 such that, in the feature space, the first feature amount V1-3 and the second feature amount V2-5 get close to each other, and the first feature amount V1-3 and the second feature amounts V2-6 and V2-7 are separated from each other. In this case, in the learning unit 25, the first and second neural networks 61 and 62 may learn such that a degree of separation between the first feature amount V1-3 and the second feature amount V2-6 is smaller than a degree of separation between the first feature amount V1-3 and the second feature amount V2-7. It should be noted that any of learning based on the relevance of the combination of the first attribute P1 and the second attribute P2 or learning based on the correspondence relationship between the teacher image and the opinion sentence in the teacher data may be performed first.

As described above, in the third embodiment, learning based on the correspondence relationship between the teacher image and the opinion sentence in the teacher data is further performed. Therefore, the first and second neural networks 61 and 62 can further learn further accurately, and as a result, it is possible to construct the first derivation model 32A and the second derivation model 33A that can derive the feature amounts with higher accuracy.

Figure 19:
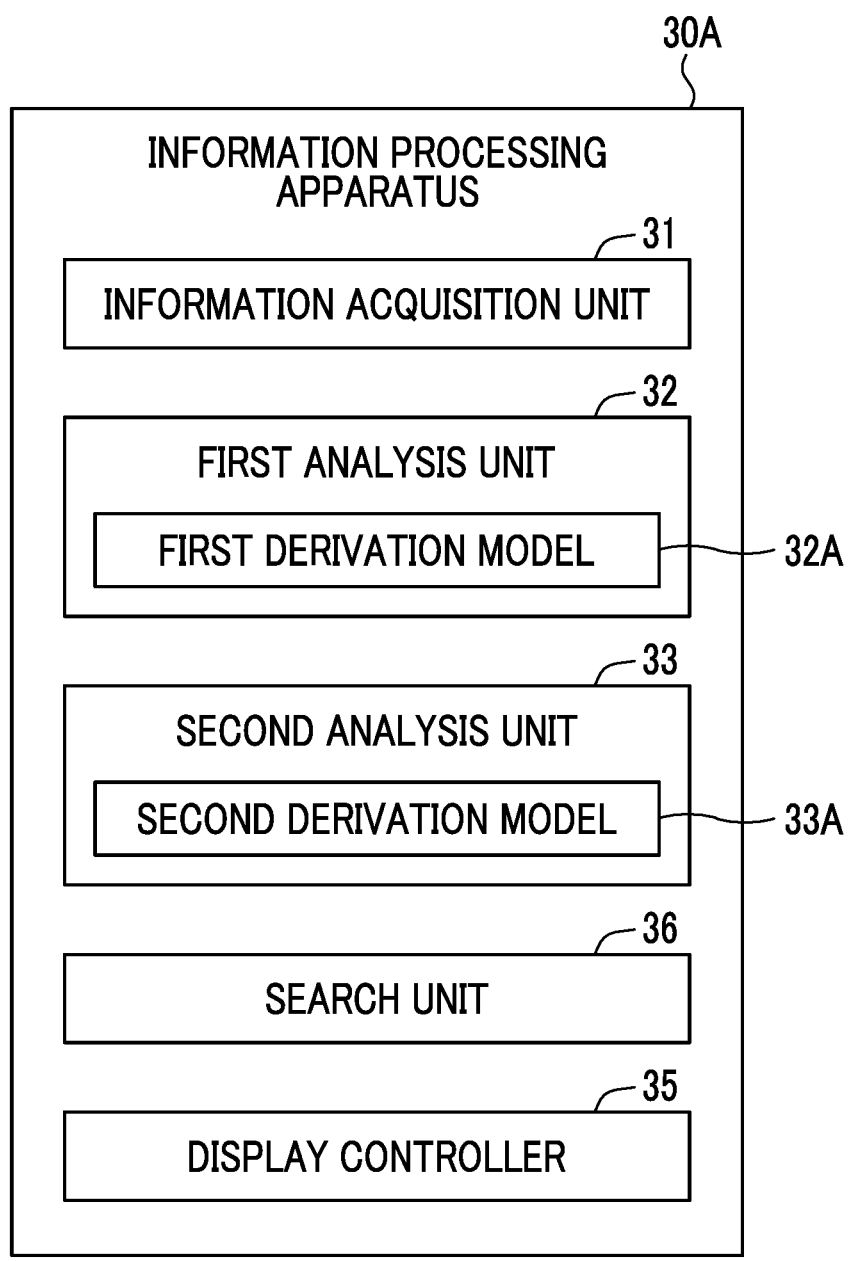
FIG. 19 is a functional configuration diagram of an information processing apparatus according to the second embodiment.

Then, the second embodiment of the information processing apparatus will be described. FIG. 19 is a functional configuration diagram of the information processing apparatus according to the second embodiment. It should be noted that, in FIG. 19, the same configurations as those in FIG. 10 are denoted by the same reference numerals, and the detailed description thereof will be omitted. As shown in FIG. 19, an information processing apparatus 30A according to the second embodiment is different from the information processing apparatus according to the first embodiment in that a search unit 36 is provided in place of the specifying unit 34.

In the information processing apparatus 30A according to the second embodiment, the information acquisition unit 31 acquires a large number of medical images stored in the image server 5. Moreover, the first analysis unit 32 derives the first feature amount V1 for each of the medical images. The information acquisition unit 31 transmits the first feature amount V1 to the image server 5. In the image server 5, the medical image is stored in the image DB 5A in association with the first feature amount V1. The medical image registered in the image DB 5A in association with the first feature amount V1 is referred to as a reference image in the following description.

In addition, in the information processing apparatus 30A according to the second embodiment, the interpretation report is generated by the interpreter interpreting the target medical image G0 in the interpretation WS 3 and inputting the opinion sentence including the interpretation result by using the input device 45. The second analysis unit 33 derives the second feature amount V2 for the input opinion sentence by analyzing the input opinion sentence using the second derivation model 33A constructed by the learning device 7 described above.

Figure 20:
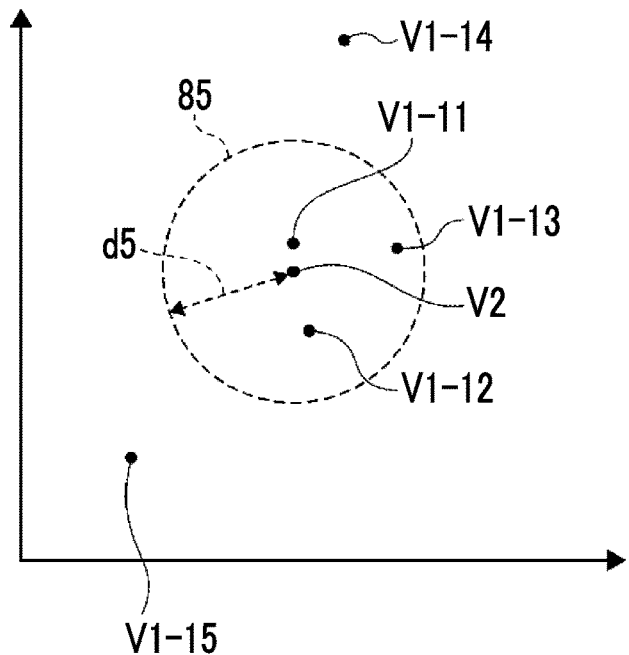
FIG. 20 is a diagram for describing a search.

The search unit 36 refers to the image DB 5A to search for the reference image associated with the first feature amount V1 having a small distance from the second feature amount V2 derived by the second analysis unit 33 in the feature space. FIG. 20 is a diagram for describing the search performed in the information processing apparatus 30A according to the second embodiment. It should be noted that, also in FIG. 20, the feature space is shown in two dimensions for the sake of description. In addition, for the sake of description, five first feature amounts V1-11 to V1-15 are plotted in the feature space.

The search unit 36 specifies the first feature amount having the distance from the second feature amount V2 within a predetermined threshold value in the feature space. In FIG. 20, a circle 85 having a radius d5 centered on the second feature amount V2 is shown. The search unit 36 specifies the first feature amount included in the circle 85 in the feature space. In FIG. 20, three first feature amounts V1-11 to V1-13 are specified.

The search unit 36 searches the image DB 5A for the reference image associated with the specified first feature amounts V1-11 to V1-13, and acquires the searched reference image from the image server 5.

Figure 21:
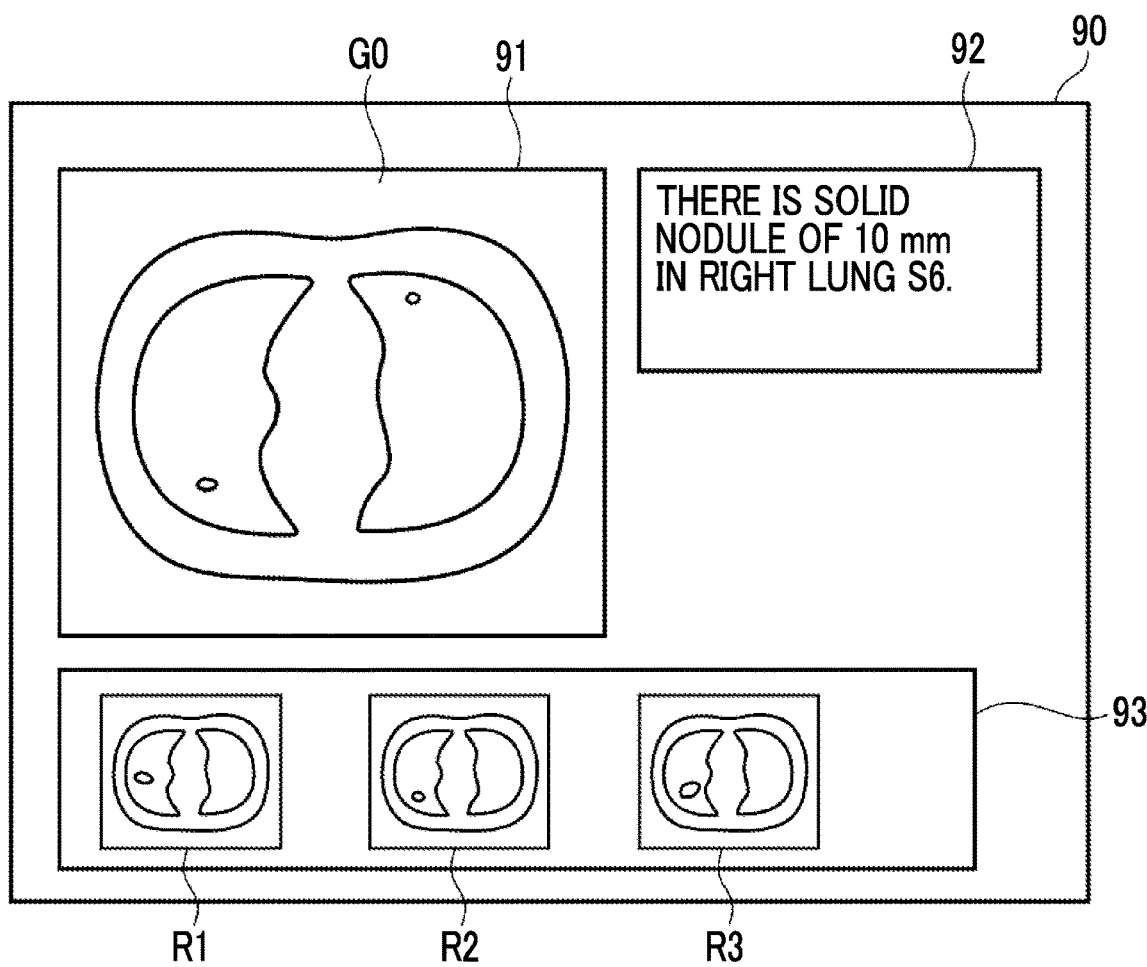
FIG. 21 is a diagram showing the display screen.

The display controller 35 displays the acquired reference image on the display 44. FIG. 21 is a diagram showing a display screen in the information processing apparatus 30A according to the second embodiment. As shown in FIG. 21, a display screen 90 includes an image display region 91, a sentence display region 92, and a result display region 93. The target medical image G0 is displayed in the image display region 91. In FIG. 21, the target medical image G0 is one tomographic image constituting the three-dimensional image of the chest. The opinion sentence input by the interpreter is displayed in the sentence display region 92. In FIG. 21, the opinion sentence of "There is the solid nodule of 10 mm in the right lung S6." is displayed.

The reference image searched by the search unit 36 is displayed in the result display region 93. In FIG. 21, three reference images R1 to R3 are displayed in the result display region 93.

Figure 22:
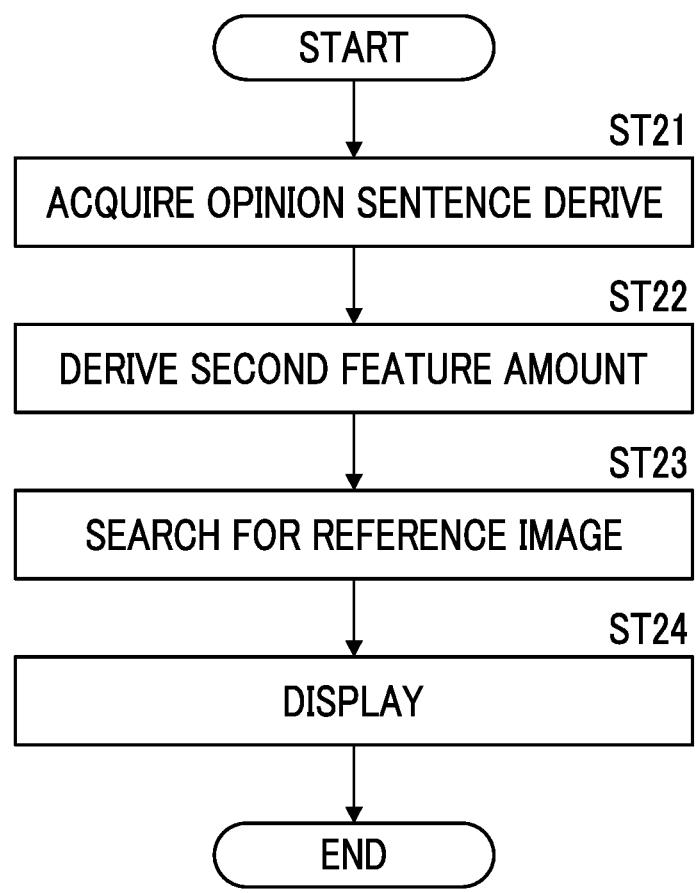
FIG. 22 is a flowchart showing information processing performed in the second embodiment.

Then, information processing according to the second embodiment will be described. FIG. 22 is a flowchart of the information processing according to the second embodiment. It should be noted that, the first feature amount of the reference image is derived by the first analysis unit 32, and a larger number of the first feature amounts are registered in the image DB 5A in association with the reference image. In addition, the target medical image G0 is displayed on the display 44 by the display controller 35. In the second embodiment, the information acquisition unit 31 acquires the opinion sentence input by the interpreter using the input device 45 (step ST21), and the second analysis unit 33 analyzes the input opinion sentence using the second derivation model 33A to derive the second feature amount V2 for the object described the input opinion sentence (step ST22).

Subsequently, the search unit 36 refers to the image DB 5A and searches for the reference image associated with the first feature amount V1 having a small distance from the second feature amount V2 (step ST23). Moreover, the display controller 35 displays the searched reference image on the display 44 (step ST24), and the processing ends.

The reference images R1 to R3 searched in the second embodiment are the medical images having similar features to the opinion sentences input by the interpreter. Since the opinion sentences relate to the target medical image G0, the reference images R1 to R3 have similar cases to the target medical image G0. Therefore, according to the second embodiment, it is possible to interpret the target medical image G0 with reference to the reference image having a similar case. In addition, the interpretation report for the reference image can be acquired from the report server 6 and used to create the interpretation report for the target medical image G0.

It should be noted that, in the first embodiment, the position of the object is used as the first attribute P1 and the second attribute P2, and in the second embodiment, the property of the object is used as the first attribute P1 and the second attribute P2, but the present disclosure is not limited to this. Both the position and the property of the object 55A included in the image 55 may be used as the first attribute P1, and both the position and the property of the object described in the sentence 56 may be used as the second attribute P2. In this case, the first and second neural networks 61 and 62 learn such that the distance between the derived first feature amount and second feature amount in the feature space to which the first feature amount and the second feature amount belong is smaller as the relevance of the combination of the first attribute P1 and the second attribute P2 for the position is higher. Further, the first and second neural networks 61 and 62 learn such that the distance between the derived first feature amount and second feature amount in the feature space to which the first feature amount and the second feature amount belong is smaller as the relevance of the combination of the first attribute P1 and the second attribute P2 for the property is higher. As a result, it is possible to construct the first derivation model 32A and the second derivation model 33A more accurately.

In addition, both the position and the property of the object 55A included in the image 55 may be used as the first attribute P1, and the first and second neural networks 61 and 62 may learn using the combination of the medical image and the interpretation report corresponding to the medical image as the teacher data, in addition to using both the position of the object included in the sentence 56 and the description of the property as the second attribute P2, as in the third embodiment.

In addition, in the embodiments described above, the first and second neural networks 61 and 62 learn such that, in the feature space, the first feature amount V1 and the second feature amount V2 get close to each other or separated from each other with the degree of the relevance of the combination of the first attribute P1 and the second attribute P2, but the present disclosure is not limited to this. For example, the first attribute P1 is the right lung S6 and the second attribute P2 is the right lung S7. The right lung S6 and the right lung S7 are not at the same position, but are anatomically adjacent to each other. In such a case, the first and second neural networks 61 and 62 may learn such that the first feature amount V1 and the second feature amount V2 are not too close to each other and not too far from each other.

In this case, the learning unit 25 trains the first and second neural networks 61 and 62 such that the distance between the first feature amount V1 and the second feature amount V2 in the feature space is equal to or larger than the threshold value $\alpha 0$ and equal to or smaller than the threshold value $\beta 0$ shown in FIG. 9. That is, a loss L3 is calculated by Expression (3) for three cases of a case in which a distance d6 between the first feature amount V1 and the second feature amount V2 in the feature space is smaller than the threshold value $\alpha 0$, a case in which the distance d6 is larger than the threshold value $\beta 0$, and a case in which the distance d6 is equal to or larger than the threshold value $\alpha 0$ and equal to or smaller than the threshold value $\beta 0$. Moreover, the first and second neural networks 61 and 62 learn such that the calculated loss L3 is reduced. As a result, even in a case in which the relevance of the combination of the attributes is neither too high nor too low, the first derivation model 32A and the second derivation model 33A can be constructed such that the first feature amount V1 and the second feature amount V2 can be derived while maintaining an appropriate distance in the feature space.

$$L3=\alpha 0-d6(d6<\alpha 0)$$

$$L3=d6-\beta 0(d6>\beta 0)$$

$$L3=0(\alpha 0 \leq d6 \leq \beta 0) \quad (3)$$

It should be noted that, in the embodiments described above, the derivation model that derives the feature amounts of the medical image and the opinion sentence of the medical image is constructed, but the present disclosure is not limited to this. For example, it is needless to say that the technology of the present disclosure can be applied to a case of constructing a derivation model that derives feature amounts of a photographic image and a sentence, such as a comment, corresponding to the photographic image.

In addition, in the embodiments described above, for example, as the hardware structure of the processing unit that executes various types of processing, such as the information acquisition unit 21, the first derivation unit 22, the second derivation unit 23, the attribute acquisition unit 24, and the learning unit 25 of the learning device 7, and the information acquisition unit 31, the first analysis unit 32, the second analysis unit 33, the specifying unit 34, the display controller 35, and the search unit 36 of the information processing apparatuses 30 and 30A, the following various processors can be used. As described above, the various processors include, in addition to the CPU which is a general-purpose processor that executes the software (program) to function as the various processing units described above, a programmable logic device (PLD), which is a processor of which a circuit configuration can be changed after manufacturing, such as a field programmable gate array (FPGA), a dedicated electric circuit, which is a processor having a circuit configuration specially designed to execute specific processing, such as an application specific integrated circuit (ASIC), and the like.

One processing unit may be composed of one of the various processors, or may be composed of a combination of two or more processors of the same type or different types (for example, a combination of a plurality of FPGAs or a combination of a CPU and an FPGA). In addition, a plurality of processing units may be composed of one processor. A first example of a configuration in which the plurality of processing units are composed of one processor includes a form in which one processor is composed of a combination of one or more CPUs and software and the processor functions as the plurality of processing units, as represented by the computer, such as a client and a server. A second example thereof includes a form in which a processor that realizes the function of the entire system including the plurality of processing units by one integrated circuit (IC) chip is used, as represented by a system on chip (SoC) or the like. In this way, the various processing units are composed of one or more of the various processors as the hardware structure.

Further, as the hardware structure of the various processors, more specifically, an electric circuit (circuitry) in which circuit elements, such as semiconductor elements, are combined can be used.

What is claimed is:

1. A learning device comprising:
   at least one processor,
   wherein the processor is configured to:
   derive a first feature amount for an object included in an image by a first neural network,
   derive a second feature amount for a sentence including description of an object by a second neural network,
   acquire each of a first attribute, which is an attribute of the object included in the image, and a second attribute, which is an attribute of the sentence, and
   construct a first derivation model that derives a feature amount for the object included in the image and a second derivation model that derives a feature amount for the sentence including the description of the object by training the first neural network and the second neural network, wherein, in response to training the first neural network and the second neural network, in a feature space to which the first feature amount and the second feature amount belong, the first attribute and the second attribute are determined as being more relevant as a distance in the feature space between the derived first feature amount and the derived second feature amount is reduced, and the first attribute and the second attribute are determined as being less relevant as the distance in the feature space between the derived first feature amount and the derived second feature amount is increased.

2. The learning device according to claim 1, wherein the first attribute is a position of the object in the image, and
the second attribute is a position of the object described in the sentence.

3. The learning device according to claim 1, wherein the first attribute is a property of the object included in the image, and
the second attribute is a property of the object described in the sentence.

4. The learning device according to claim 3, wherein the processor is configured to acquire the first attribute and the second attribute based on a co-occurrence relationship of a text representing the property.

5. The learning device according to claim 1, wherein
the distance between the derived first feature amount and the derived second feature amount in the feature space is reduced in a case in which the object included in the image and the object described in the sentence correspond to each other, and
the distance between the derived first feature amount and the derived second feature amount in the feature space is increased in a case in which the object included in the image and the object described in the sentence do not correspond to each other.

6. The learning device according to claim 1, wherein the image is a medical image,
the object included in the image is a lesion included in the medical image, and
the sentence is an opinion sentence in which an opinion about the lesion is described.

7. An information processing apparatus comprising:
at least one processor,
wherein the processor is configured to:
derive the first feature amount for one or more objects included in a target image by the first derivation model constructed by the learning device according to claim 1,
derive the second feature amount for one or more target sentences including description of an object by the second derivation model constructed by the learning device according to claim 1,
specifies specify the first feature amount corresponding to the second feature amount based on the distance between the derived first feature amount and the derived second feature amount in the feature space, and
display the object from which the specified first feature amount is derived, in distinction from other regions in the target image.

8. An information processing apparatus comprising:
at least one processor,
wherein the processor is configured to:
receive input of a target sentence including description of an object,
derive the second feature amount for the input target sentence by the second derivation model constructed by the learning device according to claim 1,
refer to a database in which the first feature amount for one or more objects included in a plurality of reference images, which is derived by the first derivation model constructed by the learning device according to claim 1, is associated with each of the reference images, to specify at least one first feature amount corresponding to the second feature amount based on the distance between the first feature amounts for the plurality of reference images and the derived second feature amount in the feature space, and
specify the reference image associated with the specified first feature amount.

9. A learning method comprising:
deriving a first feature amount for an object included in an image by a first neural network;
deriving a second feature amount for a sentence including description of an object by a second neural network;
acquiring each of a first attribute, which is an attribute of the object included in the image, and a second attribute, which is an attribute of the sentence; and
constructing a first derivation model that derives a feature amount for the object included in the image and a second derivation model that derives a feature amount for the sentence including the description of the object by training the first neural network and the second neural network, wherein, in response to training the first neural network and the second neural network, in a feature space to which the first feature amount and the second feature amount belong, the first attribute and the second attribute are determined as being more relevant as a distance in the feature space between the derived first feature amount and the derived second feature amount is reduced, and the first attribute and the second attribute are determined as being less relevant as the distance in the feature space between the derived first feature amount and the derived second feature amount is increased.

10. An information processing method comprising:
deriving the first feature amount for one or more objects included in a target image by the first derivation model constructed by the learning method according to claim 9;
deriving the second feature amount for one or more target sentences including description of an object by the second derivation model constructed by the learning method according to claim 9;
specifying the first feature amount corresponding to the second feature amount based on the distance between the derived first feature amount and second feature amount in the feature space; and
displaying the object from which the specified first feature amount is derived, in distinction from other regions in the target image.

11. An information processing method comprising:
receiving input of a target sentence including description of an object;
deriving the second feature amount for the input target sentence by the second derivation model constructed by the learning method according to claim 9;
referring to a database in which the first feature amount for one or more objects included in a plurality of reference images, which is derived by the first derivation model constructed by the learning method according to claim 9, is associated with each of the reference images, to specify at least one first feature amount corresponding to the second feature amount based on the distance between the first feature amounts for the plurality of reference images and the derived second feature amount in the feature space; and specifying the reference image associated with the specified first feature amount.

12. A non-transitory computer-readable storage medium that stores a learning program causing a computer to execute:

a procedure of deriving a first feature amount for an object included in an image by a first neural network;

a procedure of deriving a second feature amount for a sentence including description of an object by a second neural network;

a procedure of acquiring each of a first attribute, which is an attribute of the object included in the image, and a second attribute, which is an attribute of the sentence; and a procedure of constructing a first derivation model that derives a feature amount for the object included in the image and a second derivation model that derives a feature amount for the sentence including the description of the object by training the first neural network and the second neural network, wherein, in response to training the first neural network and the second neural network, in a feature space to which the first feature amount and the second feature amount belong, the first attribute and the second attribute are determined as being more relevant as a distance in the feature space between the derived first feature amount and the derived second feature amount is reduced, and the first attribute and the second attribute are determined as being less relevant as the distance in the feature space between the derived first feature amount and the derived second feature amount is increased.

13. A non-transitory computer-readable storage medium that stores an information processing program causing a computer to execute:

a procedure of deriving the first feature amount for one or more objects included in a target image by the first derivation model constructed by the learning program according to claim 12;

a procedure of deriving the second feature amount for one or more target sentences including description of an object by the second derivation model constructed by the learning program according to claim 12;

a procedure of specifying the first feature amount corresponding to the second feature amount based on the distance between the derived first feature amount and second feature amount in the feature space; and a procedure of displaying the object from which the specified first feature amount is derived, in distinction from other regions in the target image.

14. A non-transitory computer-readable storage medium that stores an information processing program causing a computer to execute:

a procedure of receiving input of a target sentence including description of an object;

a procedure of deriving the second feature amount for the input target sentence by the second derivation model constructed by the learning program according to claim 12;

a procedure of referring to a database in which the first feature amount for one or more objects included in a plurality of reference images, which is derived by the first derivation model constructed by the learning program according to claim 12, is associated with each of the reference images, to specify at least one first feature amount corresponding to the second feature amount based on the distance between the first feature amounts for the plurality of reference images and the derived second feature amount in the feature space; and a procedure of specifying the reference image associated with the specified first feature amount.

* * * * *